United States Patent [19]

Hargreaves et al.

[11] Patent Number: 5,223,505

[45] Date of Patent: Jun. 29, 1993

[54] PYRIMIDINE DERIVATIVES

[75] Inventors: Rodney B. Hargreaves, Poynton; Paul W. Marshall, Congleton; Bernard J. McLoughlin, Broken Cross; Stuart D. Mills, Gawsworth, all of Great Britain

[73] Assignee: Imperial Chemical Industries Plc, London, England

[21] Appl. No.: 513,304

[22] Filed: Apr. 20, 1990

[30] Foreign Application Priority Data

Apr. 21, 1989 [GB] United Kingdom ................ 8909054
May 8, 1989 [GB] United Kingdom ................ 8910548

[51] Int. Cl.$^5$ ................ C07D 239/42; C07D 239/48; A61K 31/505
[52] U.S. Cl. ................ 514/275; 514/256; 514/213; 514/232.2; 514/232.5; 514/235.2; 514/235.8; 544/122; 544/123; 544/284; 544/291; 544/293; 544/323; 544/324; 544/326; 544/328; 544/82; 544/80; 544/253; 544/327; 540/593
[58] Field of Search ................ 514/256, 213, 232.2, 514/232.5, 235.2, 235.8, 275; 544/122, 123, 284, 291, 293, 323, 324, 328, 326, 82, 80, 253, 327; 540/593

[56] References Cited

U.S. PATENT DOCUMENTS 2,784,124  5/1956  Burtner .................. 260/256.4

FOREIGN PATENT DOCUMENTS 0139613A  8/1984  European Pat. Off. .

OTHER PUBLICATIONS

William A. Denny, et al., *J. Med. Chem.* (1979), 22(2), 134–150.
G. J. Atwell, et al., *J. Med. Chem.* (1968), 11, 690–694.

*Primary Examiner*—John M. Ford
*Attorney, Agent, or Firm*—Cushman Darby & Cushman

[57] ABSTRACT

This invention concerns novel aminopyrimidinium salts of the formula I:

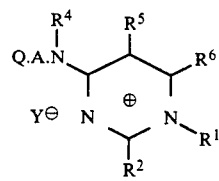

in which $R^1$ is alkyl, alkenyl, cycloalkyl, phenyl, phenylalkyl or cycloalkyl-alkyl; one of $R^2$ and $R^6$ is a basic group selected from amino, alkylamino, dialkylamino of up to eight carbon atoms, pyrrolidino, piperidino and morpholino; and the other of $R^2$ and $R^6$ is hydrogen, alkyl, alkenyl, alkoxyalkyl, phenyl, phenylalkyl, cycloalkyl or cycloalkyl-alkyl; or both of $R^2$ and $R^6$ are basic groups as mentioned above; and $R^5$ is hydrogen, (1-4C)alkyl or (3-6C)alkenyl; or $R^2$ is a basic group as mentioned above, and $R^5$ and $R^6$ together form alkylene or, together with the appendant carbon atoms of the pyrimidine ring, complete a benzene ring; $R^4$ is hydrogen, alkyl, cycloalkyl-alkyl, alkenyl, alkynyl or phenylalkyl; or $R^4$ is an optionally substitutued alkylene or alkenylene linked to the nitrogen atom of the group Q.A.N—, either of which linking groups may thereby completing a ring including two adjacent carbon atoms of Q, the carbon atoms of A and the adjacent nitrogen atom of the group —A.N—; A is a direct bond to the the group —N($R^4$)— or is alkylene or oxyalkylene; Q is a pyridyl, furyl, thienyl or phenyl moiety; and Y is a physiologically acceptable anion; but excluding a number of compounds specified hereinafter.

The invention also includes certain closely related anhydro-base derivatives which, like the formula I compounds, possess beneficial effects on the cardiovascular system (and in particular beneficial effects modulated via the sino-atrial node). Also included are pharmaceutical compositions containing the formula I compound (or a related anhydro-base) as active ingredient, and processes for the manufacture of the various novel compounds.

16 Claims, No Drawings

U.S. PATENT DOCUMENTS

| | | | |
|---|---|---|---|
| 2,845,425 | 7/1958 | Whitehead et al. | 260/256.4 |
| 4,339,453 | 7/1982 | Grier et al. | 424/251 |
| 4,725,600 | 2/1988 | Takaya et al. | 514/264 |

FOREIGN PATENT DOCUMENTS

| | | |
|---|---|---|
| 0168262A | 7/1985 | European Pat. Off. . |
| 0322133A | 12/1988 | European Pat. Off. . |
| 1241832 | 6/1067 | Fed. Rep. of Germany . |
| 3717480A | 12/1988 | Fed. Rep. of Germany . |
| 658205 | 10/1949 | United Kingdom . |
| 815833A | 9/1957 | United Kingdom . |
| 1020306A | 9/1964 | United Kingdom . |
| 1229413 | 6/1967 | United Kingdom . |
| 1502912 | 5/1974 | United Kingdom . |

PYRIMIDINE DERIVATIVES

TECHNICAL FIELD

This invention concerns novel heterocyclic compounds and, more particularly, novel aminopyrimidine derivatives which possess beneficial effects on the cardiovascular system (and in particular beneficial effects modulated via the sino-atrial node), pharmaceutical compositions containing such a derivative as active ingredient, and processes for the manufacture of and medical use of the said derivatives.

BACKGROUND TO INVENTION

Although numerous compounds are known to have medically useful effects on the cardiovascular system, hitherto there have not existed satisfactory agents which modulate the action of the sino-atrial node in warm-blooded animals such as man in a beneficial, selective and medically useful manner so that the agents are useful in treating cardiovascular disorders associated with an inappropriately elevated heart rate (that is by having a bradycardic effect) and yet have minimal effects on other haemodynamic parameters such as blood pressure or cardiac output. It is an object of the invention to provide such an agent which has inter alia bradycardic properties.

Pyrimidine derivatives have been extensively studied in the search for new pharmacologically active agents. A series of aminopyrimidine derivatives has been described as having cardiotonic properties (U.S. patent application Ser. No. 4,725,600). Various 4-aminopyrimidinium salts have been described as anti-fungal and anti-bacterial agents (U.S. patent application Ser. No. 4,339,453). The present invention is based on the unexpected and beneficial sino-atrial node modulatory effects of a novel series of aminopyrimidine derivatives of formula I defined below.

DISCLOSURE OF INVENTION

According to the invention these is provided an aminopyrimidine derivative of the formula I (set out hereinafter, together with the other chemical formulae appearing herein) wherein: $R^1$ is (1–10C)alkyl, (3–6C)alkenyl, (4–7C)cycloalkyl, phenyl, phenyl(1–4C)alkyl or (3–6C)cycloalkyl-(1–4C)alkyl; one of $R^2$ and $R^6$ is a basic group selected from amino, (1–6C)alkylamino, dialkylamino of up to eight carbon atoms, pyrrolidino, piperidino and morpholino; and the other of $R^2$ and $R^6$ is hydrogen, (1–6C)alkyl, (3–6C)alkenyl, (1–4C)alkoxy(1–4C)alkyl, phenyl, phenyl(1–4C)alkyl, (3–6C)cycloalkyl or (3–6C)cycloalkyl-(1–4C)alkyl; or both of $R^2$ and $R^6$ are basic groups independently selected from the above defined basic groups; and $R^5$ is hydrogen, (1–4C)alkyl or (3–6C)alkenyl;

or $R^2$ is a basic group as defined above, and $R^5$ and $R^6$ together form (3–6C)alkylene or, together with the appendant carbon atoms of the pyrimidine ring, complete a benzene ring;

$R^4$ is hydrogen, (3–6C)cycloalkyl-(1–4C)alkyl, (1–6C)alkyl, (3–6C)alkenyl, (3–6C)alkynyl or phenyl(1–4C)alkyl; or $R^4$ is a (1–4C)alkylene or (2–4C)alkenylene linked to the nitrogen atom of the group Q.A.N—, either of which linking groups may optionally bear a (1–4C)alkyl, phenyl or phenyl(1–4C)alkyl substituent and either of which linking groups thereby completing a ring including two adjacent carbon atoms of Q, the carbon atoms of A and the adjacent nitrogen atom of the group —A.N—; A is a direct bond to the the group —N($R^4$)— or is (1–6C)alkylene or is oxy(2–6C)alkylene in which the oxy group is at least 2 carbon atoms away from the group —N($R^4$)—; Q is a pyridyl, furyl, thienyl or phenyl moiety;

Y is a physiologically acceptable anion;

and wherein any one or more of said phenyl or benzene moieties may optionally be unsubstituted or bear one or more substituents independently selected from halogeno, (1–4C)alkyl, (3–6C)alkenyl, (1–4C)alkoxy, cyano, trifluoromethyl, nitro, carboxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy;

but excluding those compounds in which:

(a) $R^1$ is alkyl, $R^2$ is amino or alkylamino, $R^4$ is hydrogen or alkyl, $R^5$ is hydrogen or alkyl, $R^6$ is hydrogen or phenyl optionally bearing an alkyl or alkoxy substituent, A is a direct link and Q is phenyl optionally bearing an alkyl or alkoxy substituent;

(b) $R^1$ is methyl or ethyl, $R^2$ is amino, $R^4$ and $R^5$ are hydrogen, $R^6$ is methyl, and Q.A— is unsubstituted phenyl; or (c) $R^1$, $R^5$ and $R^6$ are methyl, $R^2$ is methylamino, $R^4$ is hydrogen and Q.A— 3,5-dimethylphenyl; $R^2$ is methylthio, $R^1$, $R^4$ and $R^6$ are methyl; and, in any of which, Y has the meaning stated above.

It will be understood that when $R^4$ is hydrogen, or when $R^2$ or $R^6$ is amino or alkylamino, the amino derivatives of the invention may exist in another tautomeric form to that depicted in formula I, or in a mixture of one or more of the possible tautomeric forms. It will also be understood that when one of the substituents in the formula I compounds contains a chiral centre, the compounds of the invention may exist in, and be isolated in, optically active or racemic form. The invention includes any tautomeric, optically active or racemic from of a compound of formula I which possesses the aforementioned beneficial pharmacological effects.

The compounds of formula I are quaternary salts and in some cases, for example, when $R^2$ or $R^6$ is alkylamino and the other of $R^2$ and $R^6$ has any of the meanings defined above, may be converted, for example by treatment with an quaternary ammonium hydroxide (and especially one in macroreticular resin form) to the corresponding non-ionic anhydro-base forms of the formula Ia or Ib, respectively, (or to a tautomeric form thereof when $R^4$ is hydrogen or when the other of the groups $R^2$ and $R^6$ is amino or alkylamino). Such non-ionic forms of the formula Ia or Ib in which alk stands for (1–6C)alkyl are provided as a further feature of the invention and may readily be reconverted to the quaternary salt form, for example, by treatment with the appropriate acid of the formula H.Y.

A particular value for $R^1$ when it is alkyl is, for example, (1–7C)alkyl, such as methyl, ethyl, propyl, butyl, pentyl or heptyl, of which values methyl and ethyl are generally preferred.

A particular value for $R^2$ or $R^6$ when it is alkyl is, for example, methyl, ethyl, propyl, butyl or isobutyl.

A particular value for $R^1$, $R^2$, $R^4$, $R^5$ or $R^6$ when it is alkenyl is, for example, allyl, but-2-enyl, but-3-enyl, 2-methyl-2-propenyl or pentenyl.

A particular value for $R^1$ when it is cycloalkyl is, for example, cyclopropyl, cyclobutyl, cyclopentyl, cyclohexyl or cycloheptyl, and for $R^2$ or $R^6$ is, for example, cyclopropyl, cyclobutyl, cyclopentyl or cyclohexyl.

A particular value for $R^1$, $R^2$, $R^4$ or $R^6$ when it is phenyl(1–4C)alkyl or for a phenyl(1–4C)alkyl substituent which is a part of $R^4$ is, for example, benzyl, 1-phenylethyl or 2-phenylethyl.

A particular value for $R^1$, $R^2$, $R^4$ or $R^6$ when it is cycloalkyl-alkyl is, for example, cyclopropyl-methyl, cylopentyl-methyl, cyclohexylmethyl or 2-(cyclohexyl)ethyl.

A particular value for $R^5$ when it is alkyl is, for example, methyl, ethyl, propyl, isopropyl or butyl.

A particular value for $R^2$ or $R^6$ when it is alkoxyalkyl is for example, methoxymethyl, ethoxymethyl, 2-methoxyethyl or 2-ethoxyethyl.

A particular value for $R^5$ and $R^6$ when together they form (3–6C)alkylene is, for example, trimethylene, tetramethylene, pentamethylene or a group of the formula —CH$_2$.C(CH$_3$)$_2$.CH$_2$— or —CH$_2$.C(CH$_3$)$_2$.CH$_2$.CH$_2$—.

A particular value for $R^4$ when it is alkyl is, for example, methyl, ethyl, propyl, isopropyl, butyl, isobutyl, sec-butyl or pentyl, of which values methyl and especially ethyl are particularly preferred.

A particular value for $R^4$ when it is alkynyl is, for example, prop-2-ynyl or but-2-ynyl.

A particular value for $R^2$ or $R^6$ when it is alkylamino is, for example, methylamino, ethylamino, propylamino or butylamino, and when it is dialkylamino is, for example, dimethylamino, diethylamino, methylpropylamino or dipropylamino.

A particular value for $R^4$ when it is alkylene or alkenylene linked to the nitrogen atom of the group Q.A.N— is for example, methylene, ethylidene, ethylene, isopropylidene, trimethylene, tetramethylene, vinylene or 1,3-propenylene; and a particular value for a substituent which may be present on such a linking group is, for example, methyl, ethyl, propyl, butyl, phenyl, benzyl, 1-phenylethyl or 2-phenylethyl (the benzene moiety of any of the last four groups themselves optionally substituted as defined above).

A particular value for A when it is alkylene is, for example, methylene, ethylene, trimethylene or tetramethylene, any of which may optionally bear one or two methyl substituents; and when it is oxyalkylene is, for example, oxyethylene, oxytrimethylene, methyleneoxyethylene or ethyleneoxyethylene, any of which may optionally bear one or two methyl substituents.

A preferred value for A is, for example, when it is a direct bond, methylene or ethylene.

Particular values for optional substituents which may be present as defined hereinabove on a phenyl or benzene moiety include, by way of example:
for halogeno, fluoro, chloro and bromo;
for alkyl, methyl, ethyl and propyl;
for alkenyl, allyl and 2-methyl-2-propenyl;
for alkoxy, methoxy, ethoxy and propoxy;
for alkylamino, methylamino and ethylamino;
for dialkylamino, dimethylamino and diethylamino;
for alkylthio, methylthio and ethylthio;
for alkylsulphinyl, methylsulphinyl and ethylsulphinyl;
for alkylsulphonyl, methylsulphonyl and ethylsulphonyl; and
for alkylenedioxy, methylenedioxy and isopropylidenedioxy.

In general, it is preferred that, when Q is a phenyl or benzene moiety it is unsubstituted or bears up to three substituents.

Specific values for Q include, for example, phenyl, 4-chlorophenyl, 4-methylphenyl, 2-nitrophenyl, 2-methylphenyl, 2-carboxyphenyl, 2-methoxyphenyl, 4-methylthiophenyl, 2,5-dinitrophenyl, 2,5-dimethylphenyl, 3,5-dimethylphenyl, 3,5-dichlorophenyl, 3,5-dibromophenyl, 3,5-dimethoxyphenyl, furyl, thienyl and pyridyl.

Specific values for the group Q.A.N($R^4$)— when $R^4$ is alkylene or alkenylene include, for example, 1-indolyl, 3-methyl-1-indolyl, 3-ethyl-1-indolyl, 3-propyl-1-indolyl, 5-bromo-1-indolyl, 5-chloro-1-indolyl, 5-fluoro-1-indolyl, 5-methyl-1-indolyl, 5-methoxy-1-indolyl, 1-indolinyl, 3-methyl-1-indolinyl, 3-ethyl-1-indolinyl, 3-isopropyl-1-indolinyl, 1,2,3,4-tetrahydro-1-quinolyl, 1,2,3,4-tetrahydro-2-isoquinolyl and 3,4-dihydro-1,4-benzoxazin-4-yl.

By way of example, a preferred value for $R^6$ is, alkylamino such as methylamino or ethylamino, for R5 is hydrogen, for Q is phenyl (optionally substituted as indicated above) and for A is a direct link.

A group of compounds of the invention which are of particular interest comprises those compounds of the formula II wherein:
Ra is (1–10C)alkyl, (3–6C)alkenyl, phenyl, phenyl(1–4C)alkyl, (3–6C)cycloalkyl or (3–6C)cycloalkyl-(1–4C)alkyl; Rb is (1–6C)alkyl, phenyl, phenyl(1–4C)alkyl, (3–6C)cycloalkyl or (3–6C)cycloalkyl-(1–4C)alkyl, amino, (1–4C)alkylamino or dialkylamino of up to 6 carbon atoms; Rc is hydrogen, (3–6C)cycloalkyl-(1–4C)alkyl, (1–6C)alkyl, (3–6C)alkenyl, (3–6C)alkynyl or phenyl(1–4C)alkyl; or Rc is (1–4C)alkylene or (2–4C)alkenylene linked to the nitrogen atom of the group Qa.Aa.N—, either of which linking groups may optionally bear a (1–4C)alkyl, phenyl or phenyl(1–4C)alkyl substituent and either of which linking groups thereby completes a ring including two adjacent carbon atoms of Qa, the atoms of Aa and the nitrogen of group —Aa.N—; Rd is hydrogen; Re and Rf are independently selected from hydrogen and (1–4C)alkyl, or together form (3–6C)alkylene; Qa is phenyl or pyridyl; Aa is a direct bond to the group —NRc—; Y is a physiologically acceptable anion; and wherein any one or more of said phenyl moieties may optionally be unsubstituted or bear one or more substituents independently selected from halogeno, trifluoromethyl, cyano, nitro, (1–4C)alkyl and (1–4C)alkoxy.

Specific values for Ra, Rb, Rc, Rd, Re, Rf, Aa and Qa include, for example, the relevant values mentioned hereinabove for $R^1$, $R^2$, $R^4$, $R^5$, $R^6$, Q and A.

A preferred value for $R^1$ or Ra is, for example, methyl, ethyl, butyl, phenyl or cyclohexyl, of which methyl is especially preferred.

A preferred value for $R^4$ or Rc is, for example, methyl or ethyl, of which ethyl is especially preferred.

A yet further group of compounds of the invention of particular interest comprises compounds of the formula II wherein Qa is phenyl; Aa is a direct bond to the group —N(Rc)—; Ra is (1–7C)alkyl or (3–6C)alkenyl; Rb is (1–4C)alkyl (such as methyl or ethyl); Rc is hydrogen, (1–6C)alkyl (such as methyl, ethyl, propyl or pentyl), (3–6C)cycloalkylmethyl (such as cyclopropylmethyl), or (3–6C)alkenyl (such as allyl or but-2-enyl); or Rc is (2–4C)alkylene (such as ethylene or trimethylene) or (2–4C)alkenylene (such as vinylene or 1,3-propenylene) completing a ring including two adjacent carbon atoms of benzene ring Qa and the nitrogen atom of the group —N(Rc)—; Rd is hydrogen or (1–4C)alkyl (such as methyl or ethyl); Re and Rf are independently selected from hydrogen and (1-4C)alkyl (such as methyl or ethyl); Y is a physiologically acceptable anion; and wherein benzene ring Qa may optionally be unsubstituted or bear one or two substituents independently selected from halogeno (such as fluoro, chloro or bromo), (1-4C)alkyl (such as methyl) and (1-4C)alkoxy (such as methoxy).

A still further group of compounds of the invention of special interest comprises compounds of the formula II wherein Qa is phenyl; Aa is a direct bond to the group —N(Rc)—; Ra is methyl or ethyl; Rb is methyl, ethyl or propyl; Rc is ethyl; or Rc is ethylene or vinylene completing an indoline or indole ring, respectively, including two adjacent carbon atoms of benzene ring Qa and the nitrogen atom of the group —N(Rc)—; Rd is hydrogen or methyl; Re is hydrogen and Rf is methyl or ethyl; Y is a physiologically acceptable anion; and wherein benzene ring Qa may optionally be unsubstituted or bear one or two substituents independently selected from halogeno (such as fluoro, chloro or bromo), (1-4C)alkyl (such as methyl) and (1-4C)alkoxy (such as methoxy).

Particular physiologically acceptable counter anions Y include, for example, halide (such as chloride, bromide or iodide), sulphate, fluoroborate, phosphate, nitrate, acetate, benzoate, butyrate, citrate, tartrate, dibenzoyltartrate, fumarate, trifluoroacetate, methosulphate and p-toluenesulphonate.

A preferred group of non-ionic anhydro-bases of the invention defined above comprises a compound of the formula IIa in which Ra, Rb, Rc, Rd, Aa and Qa have any of the meanings defined above and alk stands for (1-4C)alkyl (especially methyl or ethyl).

Compounds of the invention which are of particular interest include the compounds described in the accompanying Examples of which, the compounds described in Examples 20, 51, 56, 145, 147-149, 151, 156 and 158 are of special interest. The latter compounds, as described herein (or, except in the case of the non-ionic anhydro-base form described in the first part of Example 56, in the form of an alternative physiologically acceptable counter anion), are provided as a further feature of the invention.

The compounds of the invention may be obtained by standard procedures of organic chemistry already known to be applicable to the preparation of structurally analogous compounds, for example those procedures described in standard reference works on the chemistry of the pyrimidines. Such procedures for the manufacture of the novel compounds of formula I are provided as a further feature of the invention and are illustrated by the following preferred processes in which the various generic radicals have any of the meanings defined hereinbefore:

a) An amino compound of the formula III is reacted with an alkylating agent of the formula $R^1.Z$ in which Z is a suitable leaving group.

A preferred value of Z is, for example, halide (especially iodide, bromide or chloride), sulphate and p-toluenesulphate.

The reaction is generally carried out by heating the alkylating agent with the compound of formula III at a temperature of, for example, 40°-120° C. and is conveniently carried out in a suitable solvent or diluent, for example, in an ether such as dioxane, tetrahydrofuran or t-butyl methyl ether.

The starting materials of formula III can be made, for example, by reaction of the corresponding halogeno pyrimidine of the formula IV wherein X is chloro or bromo with the appropriate amine of the formula $Q.A.N(R^4)H$ at a temperature in the range, for example, 40°-150° C. this particular reaction may be carried out in the presence of a suitable solvent or diluent such as a (1-4C)alkanol or N,N-dimethylformamide, or as a melt of the reagents alone. The amines of the formula $Q.A.N(R^4)H$ and the compounds of formula IV are in general known or may be made by conventional techniques well known in the art of organic and pyrimidine chemistry.

Although it will be appreciated that in principle it is possible for alkylation to occur on either of the endocyclic nitrogen atoms, in general alkylation takes place predominantly on the nitrogen shown bearing $R^1$ in formula I and any small amount of the alternative isomer may be removed by well known methods for the purification of organic compounds, for example by chromatographic means or by fractional crystallisation. The principle exception to this is, those compounds of formula III in which $R^6$ is a tertiary amino group and $R^2$ is other than alkylamino, which compounds alkylate under the conditions of process (a) predominantly on the nitrogen atom numbered N(3) and for which values of $R^2$ and $R^6$, the corresponding compounds of formula I are best prepared by process (b) or (c) hereinafter. The position of alkylation can be established by standard techniques, for example by studies of the nuclear Overhauser effect on the proton magnetic resonance of the sample concerned.

b) A pyrimidinium salt of the formula V wherein X is a suitable leaving group is reacted with an amine of the formula $Q.A.N(R^4)H$.

The process will be seen to be analogous to that described above for the production of the starting materials of the formula IV and analogous conditions may in general be used. Thus, the process is generally carried out at an elevated temperature in the range, for example, 20°-150° C. and in the presence of a suitable solvent or diluent such as a (1-4C)alkanol or N,N-dimethylformamide.

A particularly suitable leaving group X is, for example, halogeno (especially chloro or bromo), dichlorophosphinoyl [—O.PO.Cl$_2$], or dibromophosphinoyl [—O.PO.Br$_2$]. The latter two groups may conveniently be introduced in situ by the reaction of the corresponding pyrimidinone with phosphorus oxychloride or oxybromide, respectively, for example as described in the accompanying Examples. [Note: it will readily be appreciated by those skilled in the art that the precise identity of the group X is not genrally critical to the process (b)].

The pyrimidinium salts of formula V may alternatively be obtained, for example, by analogy with process (a) above, that is by reaction of a halogeno pyrimidine of the formula IV with the appropriate alkylating agent of the formula $R^1.Z$ and in particular an iodide or bromide of the formula $R^1.I$ or $R^1.Br$. The pyrimidinones may themselves be obtained by standard procedures, for example when $R^1$ is phenyl and the like, as described in connection with Examples 1-8 hereinafter.

c) For those compounds wherein $R^6$ is amino, alkylamino or dialkylamino as defined above, a pyrimidinium salt of the formula VI wherein X is a suitable leaving group is reacted with the appropriate amine selected from ammonia, (1-6C)alkylamine, dialkylamine of up to 6 carbon atoms, pyrrolidine, piperidine and morpholine, or a salt thereof with a (1-4C)alkanoic acid (such as acetic acid).

The process will be seen to be analogous to process (b) described above and analogous considerations and reaction conditions may in general be used. In general an excess of the starting amine or an alkanoic acid salt thereof will be used. The starting compounds of formula VI may be obtained in a generally similar manner to those for the formula V compounds.

It will be appreciated that the counter anion $Y^-$ in the formula I compounds may readily be changed, for example, by reaction of the formula I compound with a suitable salt such as a silver salt or by ion-exchange chromatography on a column of a basic macroreticular resin in the form of its salt with the desired counter anion, or another conventional method. When the non-ionic anhydro-base form of a compound of I is required, (for example a compound of formula Ia, Ib or IIa), it may be obtained, for example, by reaction of the appropriate compound of formula I in which one of $R^2$ and $R^6$ is alkylamino, with a macroreticular resin containing quaternary ammonium hydroxide groups. The process is conveniently carried out by exposing a solution of the compound of formula I in an aqueous solvent such as an aqueous (1-4C)alkanol (for example methanol, ethanol or 2-propanol) to the resin at or near ambient temperature, for example by trickling the solution over a bed or through a column of the resin. The anhydo-base form may then conveniently be returned to an ionic form of formula I by recation with the appropriate acid of formula H.Y.

It will also be appreciated that certain of the various optional substituents in the compounds of the invention may be introduced by standard aromatic substitution reactions or generated by conventional functional group modifications either prior to or immediately following process (a), (b) or (c) above, and as such are included in the process aspect of the invention. Such reactions and modifications include, for example, introduction of nitro or halogeno, reductive alkylation of nitro, oxidation of alkylthio to alkylsulphinyl or alkylsulphonyl and reduction of alkynyl or alkenyl. The reagents and reaction conditions for such procedures are well known in the chemical art.

As indicated above, the compounds of the invention possess useful pharmacological properties and modulate the action of the sino-atrial node in warm-blooded animals in a beneficial, selective and medically useful manner so that the agents are useful in treating cardiovascular disorders associated with an inappropriately elevated heart rate and with minimal effects on other haemodynamic parameters such as blood pressure or cardiac output. The beneficial and selective effects of the cardiovascular system may be demonstrated using one or more of the following standard laboratory techniques.

a) Bradycardic effect (reduction in beating rate of the spontaneously beating isolated guinea pig right atrium).

This technique involves the dissection of the right atrium from a guinea pig heart, taking care not to damage the sino-atrial node region. The atrium is established in oxygenated (95% $O_2$; 5% $CO_2$) Tyrode's solution [containing 8.0 g NaCl, 0.19 g KCl, 0.025 g $MgCl_2$, 0.05 g $NaH_2PO_4$, 1.0 g $NaHCO_3$, 0.2 g $CaCl_2$ and 2.7 g glucose, per liter of deionised water] between two platinum spikes which are connected via an amplifier to a conventional rate-meter, triggered by the action potentials across the atrium. The preparation is bathed in oxygenated Tyrode's solution at 37 degrees Celsius and allowed to equilibrate for 30 minutes before the addition of a solution of the test compound in a mixture of dimethyl sulphoxide and Cremophor EL, diluted as required with Tyrode's solution. Further solutions of test compound are then added cumulatively at 15 minute intervals or when a steady-state beating rate has been attained. This enables an $IC_{20}$ (i.e. the micromolar concentration required to reduce the beating rate by 20%) to be calculated. Typically, a compound of formula I will have an $IC_{20}$ of 10 micromolar or less.

b) Effect on contractile force of electrically stimulated isolated guinea pig left atrium.

This technique involves the dissection of the left atrium from a guinea pig heart into oxygenated Tyrode's solution. The atrium is then clamped in a polyacrylate plastic holder containing two stainless steel stimulating electrodes. The free end of the atrium (normally the atrial appendage) is attached with silk thread to an isometric force transducer. The atrium is then set under a resting tension of 1 g and is allowed to equilibrate in oxygenated Tyrode's solution for 20 minutes before being stimulated into beating by application of 2.5 Hz, 3 mS pulses at 1.5 times the threshold voltage (normally in the range 3–7 V). A solution ($10^{-5}$M or less) of the test compound [made up essentially as in (a) above, but using physiological saline solution in place of Tyrode's solution] is then added and the effect on contractile force measured. In this way a comparison of the effect with that of a control solution without any test compound can be obtained. Typically, at a concentration in the range 1–30 micromolar compounds of the formula I show <15% reduction in contractile force.

c) Bradycardic effect in the anaesthetised rat

This technique involves the use of Wistar rats (Alderley Park strain) which are pre-anaesthetised by intravenous injection of alphaxalone/alphadalone (1.5 ml per kg). A polyethylene cannula is inserted into the jugular vein and anaesthesia is maintained by infusion of alphaxalone/alphadalone at a rate of 0.025–0.12 ml per kg per minute. A polyethylene cannula is also inserted into the carotid artery and connected to a pressure transducer filled with physiological saline solution. The arterial blood pressure signal is used to trigger an internally calibrated heart rate meter and the transducer is calibrated with a mercury manometer. The output of the heart rate meter and of the pressure transducer are then recorded simultaneously on a standard chart recorder. After cannulation, the rat preparation is allowed to stabilise for 10 minutes. A solution of a test compound [made up as in (a) above, in a volume of 1 ml per kg] is then administered via the venous cannula in four cumulative doses separated by 5 minute intervals. A group of five rats is used for each test compound. The effects on heart rate and blood pressure may then be determined in comparison with those of a control injection. Typically, a compound of formula I active using this procedure will require an i.v. dose of 5 mg/kg or less to produce a 30% reduction in heart rate (i.e. the $ED_{30}$ dose).

The beneficial effects of a test compound on the cardiovascular system, such as bradycardic effects without an adverse effect on heart force, blood pressure and or cardiac output, may also be determined in anaesthetised dogs and in dogs in which tachycardia has been induced by exercise. In general, the compounds of the invention show significant and predominantly selective bradycardic effects as evidenced by activity in at least two of the above mentioned test techniques. No overt toxicity is generally observed with the compounds of formula I in the above in vivo test techniques at doses several multiples of those at which significant bradycaridc effects are seen.

By way of illustration, the compound described hereinafter in Example 51 had an $IC_{20}$ of about $10^{-6}M$ in procedure (a) and had an $ED_{30}$ of 0.3 mg/kg i.v. for reduction of heart rate in procedure (c). Other compounds of formula I exemplified hereinafter will in general show activity of the same general order.

When used in the treatment of diseases of the cardiovascular system, such as myocardial ischaemia affecting warm-blooded animals (and in particular man), it is envisaged that a compound of formula I will be administered orally, intravenously or by some other medically acceptable route (such as by inhalation, insufflation, sub-lingual or transdermal means) so that a dose in the general range, for example, 0.01 mg to 10 mg per kg body weight is received. However, it will be understood that the precise dose administered will necessarily vary according to the nature and severity of the disease and the age and sex of the patient being treated.

In general, the pyrimidinium salts of formula I (or the related non-ionic anhydro-bases) will usually be administered in the form of a pharmaceutical composition, that is, together with a pharmaceutically acceptable diluent or carrier and such a composition is provided as a further feature of the invention. It will be recognised that it may be convenient to produce a particular pyridinium salt of formula I in situ, by using the sppropriate anhydro-base and incorporating an acid of the formula HX during the production of a particular formulation.

A composition of the invention may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose form containing, for example, 5–200 mg of the compound of formula I.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate) to minimise dissolution of the active ingredient of formula I in the stomach or to mask unpleasant taste.

The compositions of the invention may also contain one or more agents known to be of value in the diseases or conditions of the cardiovasculature intended to be treated. Thus, they may contain, in addition to the compoound of formula I, for example, one or more other known agents selected from platelet aggregation inhibitors, prostanoid constrictor antagonists or synthase inhibitors (such as thromboxane $A_2$ antagonists or synthase inhibitors), cyclooxygenase inhibitors, hypolipidemic agents, anti-hypertensive agents (such as an angiotensin converting enzyme inhibitors, renin inhibitors or angiotensin antagonists), inotropic agents. $\beta$-adrenergic antagonists, thrombolytic agents, vasodilators and calcium channel antagonists.

In addition to their use in therapeutic medicine, the compounds of formula I are also useful as pharmacological tools in the development and standardisation of test systems for the evaluation of the new cardiovascular agents in laboratory animals such as cats, dogs, rabbits, monkeys, rats and mice.

The invention will now be illustrated by the following non-limiting Examples in which, unless otherwise stated:

(i) evaporations were carried out by rotary evaporation in vacuo;

(ii) operations were carried out at room temperature, that is in the range 18°–26° C.;

(iii) flash column chromatography or medium pressure liquid chromatography (MPLC) was performed on silica gel [either Fluka Kieselgel 60 (catalogue no. 60738) obtained from Fluka AG, Buchs, Switzerland, or Merck Kieselgel Art. 9385, obtained from E Merck, Darmstadt, Germany];

(iv) yields are given for illustration only and are not necessarily the maximum attainable by diligent process development;

(v) proton NMR spectra were normally determined at 200 MHz in deuterated dimethyl sulphoxide as solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;

(vi) all end-products were characterised by microanalysis, NMR and/or mass spectroscopy; and (vii) conventional abbreviations are used for individual radicals and recrystallisation solvents, for example, Me=methyl, Et=ethyl, Pr=Propyl, $Pr^i$=isopropyl, Bu=butyl, $Bu^i$=isobutyl, Ph=phenyl; EtOAc=ethyl acetate, $Et_2O$=ether, MeCN=acetonitrile, MeOH=methanol, EtOH=ethanol, $Pr^iOH$=2-propanol, $H_2O$=water.

EXAMPLE 1

A mixture of 1,4-dihydro-1-heptyl-6-methyl-2-methylamino-4-pyrimidinone monohydrate (0.75 g, 2.9 mM) and phosphorus oxychloride (3.5 ml, an excess) was heated at a bath temperature of 130° C. for 2.5 hours. Excess phosphorus oxychloride was removed by evaporation. The residue was mixed with toluene (20 ml) and the volatile material evaporated. The procedure was repeated with a further portion of toluene (20 ml) to give 4-chloro-1-heptyl-6-methyl-2-methylaminopyrimidinium chloride as a crude solid. This material was mixed with ethanol (5 ml) and N-methylaniline (0.8 g, 7.5 mM). The solution obtained was heated at reflux for 2.5 hours. The ethanol was removed by evaporation and water (10 ml) was added to the residue. The aqueous mixture was extracted with ether (4×10 ml) and the extracts were discarded. The aqueous phase was extracted with methylene chloride (4×10 ml). Water was removed from these extracts by filtration through phase-separating filter paper and the solvent was evaporated. The brown, oily residue obtained crystallised on trituration with ether to give a white solid (0.742 g). This solid was recrystallised from acetone-ether to give 1-heptyl-6-methyl-2-methylamino-4-N-methylanilinopyrimidinium chloride as a crystalline solid (0.49 g, 46% yield), m.p. 154°–155° C.; microanalysis, found: C,65.7; H,8.6; N,14.9%; $C_{20}H_{31}N_4Cl.0.25\ H_2O$ requires C,65.3; H,8.6; N,15.2%; NMR: 0.9(3H,t,$CH_3$), 1.3[10H,complex,$(CH_2)_5$], 2.36(3H,s,CH$_3$), 2.9(3H,br,NCH$_3$), 3.5(3H,s,N-CH$_3$), 4.0(2H,t,NCH$_2$), 5.8(1H,br,aromatic), 7.4–7.6(5H,complex,aromatic), 8.65(1H,br,NH).

EXAMPLE 2

The procedure described in Example 1 was repeated using N-ethylaniline. There was thus obtained 4-N-ethylanilino-1-heptyl-6-methyl-2-methylaminopyrimidinium chloride (0.527 g, 48% yield), m.p. 126°–128° C.; microanalysis, found: C,66.7; H,9.0; N,14.5%: C$_{21}$H$_{33}$N$_4$Cl requires C,66.9; H,8.8; N,14.9%: NMR: 0.87(3H,t,CH$_3$), 1.2(3H,t,CH$_3$), 1.26[10H,complex,(CH$_2$)$_5$], 2.3(3H,s,CH$_3$), 3.0(3H,br,NCH$_3$), 4.0(4H,complex,NCH$_2$), 5.6(1H,br,aromatic) 7.3–7.6(5H,complex,aromatic).

The pyrimidinone starting material for Examples 1 and 2 was prepared as follows:

(i) A solution of heptylamine (9.66 g, 84 mM) in methylene chloride (30 ml) was added dropwise to a stirred suspension of 2H-3,4-dihydro-6-methyl-2-thioxo-1,3-oxazin-4-one (6 g, 42 mM) in methylene chloride (120 ml). The resulting solution was left at ambient temperature for 16 hours and the solvent removed by evaporation. A mixture of the residue in acetic acid (20 ml) was heated under reflux for 30 minutes. The solvent was removed by evaporation and the residue purified by flash column chromatography on Fluka Kieselgel 60 using ether as eluant to give 2,3-dihydro-1-heptyl-6-methyl-2-thioxo-4(1H)-pyrimidinone as a solid having a satisfactory microanalysis.

(ii) The thioxo compound (2.42 g, 1.01 mM) from (i) above in acetonitrile (30 ml) and methyl iodide (4 ml, an excess) was heated under reflux for 8 hours. The solvent was removed by evaporation and the residue was shaken with a mixture of methylene chloride (20 ml) and saturated aqueous sodium carbonate solution (30 ml). The organic layer was washed with water (20 ml) and water removed by filtration through phase-separating filter paper. Removal of the solvent by evaporation gave an oily residue, which slowly solidified to give 1,4-dihydro-1-heptyl-6-methyl-2-methylthio-4-pyrimidinone (2.2 g) as a solid which was used without further purification.

(iii) Methylammonium acetate (14 g, an excess) was added to the methylthio compound (2.2 g) from (ii) above. The mixture was heated at a bath temperature of 175°–180° C. for 0.5 hours and allowed to cool. Water (10 ml) was added and the oily mixture was extracted with methylene chloride (4×10 ml). Water was removed from the extracts by filtration through phase-separating filter paper. Evaporation of the solvent left a residue, which was treated with water (10 ml). The crystalline solid which was precipitated was collected by filtration, washed with water, and recrystallised from ethyl acetate to give 1,4-dihydro-1-heptyl-6-methyl-2-methylamino-4-pyrimidinone monohydrate (1.68 g, 65% yield), m.p. 100°–103° C.; microanalysis, found: C,61.5; H,9.8; N,16.7%; C$_{13}$H$_{22}$N$_3$O.H$_2$O requires: C,61.4; H,9.4; N,16.5%.

EXAMPLES 3–8

The procedure described in example 1 was repeated using the appropriate 4-chloro-1-substituted-pyrimidine derivative of the formula V (X=Cl) [obtained in situ from the corresponding 4-pyrimidinone] and the appropriate aniline. There were thus obtained the following compounds of the formula I (R$^5$=H, R$^6$=CH$_3$, A=-direct bond, Q=phenyl, Y=Cl$^-$):

| Hydration | Example | R$^1$ | R$^2$ | R$^4$ | m.p. °C. | yield (%) (recryst. solvent) |
|---|---|---|---|---|---|---|
| — | 3 | cyclohexyl | NH$_2$ | Et | 219–220 | 34 (Me$_2$CO/Et$_2$O) |
| 0.25 H$_2$O | 4 | phenyl | NHMe | Me | 227–228 | 37 (Me$_2$CO) |
| 1.0 H$_2$O | 5 | phenyl | NHMe | Et | 128–129 | 15 (EtOAc) |
| 1.33 H$_2$O | 6 | phenyl | NH$_2$ | Me | 125–127 | 8 (Me$_2$CO/Et$_2$O) |
| 0.25 H$_2$O | 7 | 4-MeO-phenyl | NH$_2$ | Et | 215–216 | 46 (Me$_2$CO/Et$_2$O) |
| 0.75 H$_2$O | 8 | phenyl | NH$_2$ | Et | 249–250 | 11 (EtOAC)/Et$_2$O |

The starting material for Example 3 was prepared as follows:

(i) Cyclohexylthiourea (27.8 g, 176 mM) and 2,6,6-trimethyl-1,3-dioxin-4-one (90%, 36 ml, 229 mM) were heated with a bath temperature of 120° C. for 2 hours. The mixture was allowed to cool and was triturated with ether. The solid obtained was purified by filtration chromatography on silica (Fluka Kieselgel 60) using methylene chloride/pentane (1:1) as eluant. The material obtained was purified by further chromatography on silica (Kieselgel 60) using ethyl acetate/pentane (1:4) as eluent. There was thus obtained 1-cyclohexyl-3-(3-oxobutanoyl)thiourea (17.7 g, 42%) as a solid, m.p. 100°–102° C.: m/e: 242(M+).

(ii) A mixture of the above thiourea (10.7 g, 44 mM) and p-toluenesulphonic acid (10.7 g, 56 mM) was heated in refluxing ethanol (80 ml) for 18 hours. The solution was cooled to 5° C. The resulting crystalline precipitate was collected by filtration to give 1-cyclohexyl-2,3-dihydro-6-methyl-2-thioxo-4(1H)-pyrimidinone (3.6 g, 36%), m.p. 240°–243° C.; microanalysis, found: C,59.1; H,7.3; N,12.4%; C$_{11}$H$_{16}$N$_2$OS requires: C,58.9; H,7.1; N,12.5%.

(iii) A mixture of the above thioxo compound (2.96 g, 13.2 mM) and methyl iodide (8.8 mL, an excess) was heated under reflux in acetonitrile (10 ml) for 5 hours. The solvent was removed by evaporation and the residue was shaken with a mixture of saturated aqueous sodium carbonate (50 ml) and ethyl acetate (50 ml). The aqueous phase was further extracted with ethyl acetate (3×50 ml). The combined extracts were dried (MgSO$_4$) and solvent removed by evaporation to give 1-cyclohexyl-1,4-dihydro-6-methyl-2-methylthio-4-pyrimidinone as a crude solid (3.1 g) which was used without further purification. [A sample from a repeat preparation was recrystallised from ethyl acetate/ petroleum ether (b.p. 60°–80° C.) to give solid of m.p. 184°–186° C. and microanalysis, found: C,60.5; H,7.9; N,11.8%; C$_{12}$H$_{18}$H$_2$OS requires: C,60.5; H,7.6; N,11.8%.]

(iv) A mixture of the above methylthio compound (3.1 g) and ammonium acetate (15 g) was heated at 180° C. (bath temperature) for 2 hours. Further portions (5 g) of ammonium acetate were added at intervals of 20 minutes. The mixture was then cooled and water (50 ml) was added. The aqueous mixture was extracted with methylene chloride (8×30 ml) and the combined organic extracts were dried (MgSO$_4$) and the solvent evaporated. The semi-solid residue was dissolved in ethanol (50 ml) and concentrated aqueous sodium hydroxide solution (5 ml). The volatile material was removed by evaporation. The residue was treated with ethanol (50 ml), followed by 2M hydrochloric acid to pH<3. The solvents were then removed from the acid mixture. The solid residue was extracted with hot methanol and the extracts clarified by filtration. The filtrate was evaporated and the residue was recrystallised first from ethanol/2-propanol (1:1 v/v) and then from ethanol. There was thus obtained 2-amino-1-cyclohexyl-1,4-dihydro-6-methyl-4-pyrimidinone hydrochloride (0.98 g, 30% based on thioxo compound), m.p. 225°–226° C., with a satisfactory microanalysis.

The starting material for Ex. 7 was prepared as follows:

N-(4-Methoxyphenyl)thiourea (18.2 g, 100 mM) and 2,6,6-trimethyl-1,3-dioxin-4-one (21.3 g, 150 mM) were heated together at 140° C. (bath temperature) for 30 minutes. The solid product was cooled, treated with ethanol (100 ml), boiled for 10 minutes, cooled and the solid product was isolated by filtration. More dioxinone (21.3 g) was added to the above material and the mixture was heated at 140° C. for a further 20 minutes. Ethanol (50 ml) was then added to the cooled mixture, which was then heated under reflux for 5 minutes. The mixture was cooled and the solid product isolated by filtration to give 2,3-dihydro-1-(4-methoxyphenyl)-6-methyl-2-thioxo-4(1H)pyrimidinone (17.9 g, 72% yield) m.p. 248°–249° C.; microanalysis, found: C,58.2; H,4.9; N,11.0%; $C_{12}H_{12}N_2OS$ requires: C,58.1; H,4.8; N,11.3%.

The methylthio pyrimidinones necessary for the preparation of Examples 4–8 were obtained in an analogous manner to that described for the equivalent starting material for Example 3:

(1) 1,4-dihydro-6-methyl-2-methylthio-1-phenyl-4-pyrimidinone (required for Examples 4–6 and 8): obtained as a solid in 67% yield, m.p. 225° C. (dec.) after trituration with acetone; and (2) 1,4-dihydro-6-methyl-1-(4-methoxyphenyl)-2-methylthio-4-pyrimidinone (required for Example 7): obtained as a solid in 73% yield, m.p. 211°–213° C. after recrystallisation from acetonitrile.

The necessary aminopyrimidinones were obtained in an analogous manner to that described for the equivalent starting material for Example 3:

(3) 1,4-dihydro-6-methyl-2-methylamino-1-phenyl-4-pyrimidinone hydrochloride (required for Examples 4 and 5): obtained as a solid, m.p. 199°–200° C. in 90% yield, after purification by flash column chromatography on silica (Kieselgel 60) using methylene chloride/methanol (9:1 v/v) as eluant:

(4) 2-amino-1,4-dihydro-6-methyl-1-phenyl-4-pyrimidinone acetate (required for Examples 6 and 8): obtained as a solid, m.p. 269°–271° C. in 42% yield, after recrystallisation from ether/acetic acid; and (5) 2-amino-1,4-dihydro-1-(4-methoxyphenyl)-6-methyl-4-pyrimidinone hydrochloride (required for Example 7): obtained as a solid, m.p. 287°–289° C. in 56% yield, after recrystallisation from ethanol.

EXAMPLE 9

A mixture of 2-amino-4-N-ethylanilinopyrimidine (2.2 mM), allyl bromide (6.5 mM) and dioxan (1 ml) was heated at 100° C. for 1.5 hours. The precipitated solid was collected by filtration, washed with dioxan and ether and then dried. There was thus obtained 1-allyl-2-amino-4-N-ethylanilinopyrimidinium iodide in 60% yield, m.p. 174°–176° C.; having a satisfactory microanalysis and NMR spectrum. [Note: the site of quaternisation was confirmed by conventional Nuclear Overhauser studies]

The pyrimidine starting material was prepared as follows:

A mixture of 4-chloro-2-aminopyrimidine (4.63 mM) and N-aniline (1.0 ml, 9.2 mM) was heated as a melt at 95°–100° C. for 15 hours. The residue was partitioned between methylene chloride (50 ml) and 2M hydrochloric acid (50 ml) and stirred for 15 minutes. The organic phase was separated and the aqueous phase was extracted again with further portions of methylene chloride (2×20 ml). The combined organic layers were washed successively with saturated sodium bicarbonate solution, water and brine (50 ml each), dried (MgSO$_4$) and then the solvent was evaporated. The residual solid was triturated with ether and hexane and separated by filtration to give 2-amino-4-N-ethylanilinopyrimidine in 17% yield, m.p. 188°–190° C.

EXAMPLES 10–12

The procedure described in Example 9 was repeated, but using the appropriate substituted pyrimidine of formula III and appropriate alkylating agent of formula $R^1.Y$ heated together for about 18 hours. The following compounds of formula I (Q=phenyl, A=direct bond, $R^5=R^6=H$) were obtained, all of which were recrystallised from methanol and ether:

| Example | $R^2$ | $R^1$ | $R^4$ | Y | m.p. (°C.) | yield (%) |
|---|---|---|---|---|---|---|
| 10 | NH$_2$ | Pr$^c$.CH$_2$ | Et | Br | 215–216 | 57 |
| 11 | NH$_2$ | benzyl | Et | Cl | 254–256 | 65* |
| 12 | NH$_2$ | allyl | Pr | Br | 175–177 | 39 |

Notes
(1) * obtained as a partial hydrate (0.25 H$_2$O).
(2) Pr$^c$.CH$_2$ stands for cyclopropylmethyl.

The necessary starting 2-amino-4-N-propylanilinopyrimidine for Example 12 was made in an analogous manner to that described for the analogous intermediate in Example 9 and was obtained as a solid, m.p. 82°–84° C. in 89% yield.

EXAMPLE 13

A solution of 2-amino-4-(indolin-1-yl)pyrimidine (212 mg; 1 mM) in warm N,N-dimethylformamide (DMF,15 ml) was treated with ethyl iodide (1 ml). The mixture was allowed to stand at ambient temperature for 15 hours and the precipitated solid was filtered and washed with ethyl acetate. There was thus obtained 1-ethyl-2-amino-4-(indolin-1-yl)pyrimidinium iodide (280 mg, 79%), m.p. >310° C.; microanalysis, found: C,44.2; H,4.8; N,15.1%; $C_{14}H_{17}N_4I.0.5H_2O$ requires; C,44.6; H,4.8; N,14.9%; NMR: 1.2–1.4(3H,t, CH$_2$CH$_3$), 3-2–3.4 (2H,t, indoline-3CH$_2$), 3.95–4.1(2H,q,CH$_2$CH$_3$), 4.1–4.3(2H,t,indoline-2CH$_2$), 6.55–6.65(1H,d,pyrimidine-5H), 7.1–7.4(3H,complex,aromatic), 8.1–8.2(1H,d,indoline-7H), 8.25–8.5 (2H,br,NH$_2$), 8.63–8.73 (1H,d, pyrimidine-6H).

The starting material was prepared as follows:

A suspension of 2-amino-4-chloropyrimidine (1.3 g; 10 mM) in dioxan (30 ml) was treated with indoline (2.4 g; 20 mM) and the mixture was heated for 18 hours at 95°–100° C. The precipitated product was separated from the cooled mixture by filtration and suspended in a mixture of 2-propanol (30 ml) and a solution of potassium hydroxide flake (6 g) in water (10 ml). This mixture was stirred and heated at 95°-100° C. for one hour. The hot 2-propanol solution was separated from the aqueous layer and allowed to cool. The solid product was recrystallised from 2-propanol to give 2-amino-4-(indolin-1-yl)pyrimidine as a solid (1.9 g, 89.6%), m.p. 177°-179° C.; microanalysis, found: C,62.2; H,6.2; N,23.8%; $C_{12}H_{12}N_4.H_2O$ requires: C, 62.6; H,6.1; N,24.3%.

EXAMPLES 14-15

The procedure described in Example 13 was repeated using propyl or heptyl iodide. There were thus obtained the following compounds:

(Example 14): 2-amino-4-(indolin-1-yl)-1-propyl-pyrimidinium iodide, as a solid, m.p. >310° C., in 42% yield; and (Example 15): 2-amino-4-(indolin-1-yl)-1-heptyl-pyrimidinium iodide, as a solid, m.p. 219°-221° C., in 57% yield.

Example 16

A mixture of 2-amino-4-(indol-1-yl)pyrimidine (210 mg, 1 mM) and methyl iodide (1 ml) in dioxan (5 ml) was heated for 2 hours at 95°-100° C. The mixture was cooled and the precipitated product was collected by filtration, washed with ethyl acetate and then crystallised from methanol. There was thus obtained 2-amino-4-(indol-1-yl)-1-methyl-pyrimidinium iodide (280 mg; 79.5%) m.p. 295°-296° C. (decomp.), microanalysis, found: C,44.3; H,3.6; N,15.5%; $C_{13}H_{13}N_4I$ requires: C,44.3; H,3.7; N,15.9%; NMR: 3.71(3H,s,N-CH$_3$), 6.95-7.05 (1H,d,indole-3H), 7.3-7.45(3H,complex,aromatic), 7.45-7.55 (1H,d,pyrimidine-5H) 7.65-7.75(1H,complex,indole-7H), 8.15-8.25 (1H,d,indole-2H), 8.45-8.55(1H,d,pyrimidine-6H), 8.8-9.5(2H,br,NH$_2$).

The indole starting material was prepared as follows:

A mixture of 2-amino-4-(indolin-1-yl)pyrimidine (2.6 g, 12 mM) and 30% w/w palladium on charcoal (260 mg) in diphenyl ether (15 ml) was heated under reflux for 2 hours. The mixture was cooled, diluted with methylene chloride (100 ml) and filtered through diatomaceous earth. The filtrate was concentrated in vacuo and the residual oil was diluted with hexane (200 ml). The precipitated solid was collected by filtration and washed with hexane. There was thus obtained 2-amino-4-(indol-1-yl)-pyrimidine (2.1 g; 81.5%), m.p. 163°-165° C.; microanalysis, found: C,68.5; H,4.6; N,26.2%; $C_{12}H_{10}N_4$ requires: C,68.6; H,4.8; N,26.7%.

EXAMPLES 17-19

The procedure described in Example 16 was repeated using ethyl, propyl or pentyl iodide as alkylating agent for 18 hours instead of 2 hours. there were thus obtained the following compounds of formula I:

(Example 17): 2-amino-1-ethyl-4-(indol-1-yl)pyrimidinium iodide, as a solid, m.p. 248°-250° C. (with decomposition), after recrystallisation from methanol and in 59% yield;

(Example 18): 2-amino-4-(indol-1-yl)-1-propyl-pyrimidinium iodide, as a solid, m.p. 256°-258° C. (with decomposition), after recrystallisation from methanol/ether and in 32% yield; and (Example 19): 2-amino-4-(indol-1-yl)-1-pentyl-pyrimidinium iodide as a solid, (isolated as a methanolate), m.p. 134°-136° C., after recrystallisation from methanol/ether and in 25% yield.

EXAMPLE 20

A mixture of 6-methyl-2-methylamino-4-N-methylanilinopyrimidine (14.01, 61.5 mM), methyl iodide (10.7 ml, 172 mM) and dioxan (140 ml) was heated at reflux for 15 hours. The mixture was cooled. The solid was collected by filtration, washed with dioxan (10 ml) and hexane (100 ml) and then recrystallised from 2-propanol. There was thus obtained 1,6-dimethyl-2-methylamino-4-N-methylanilinopyrimidinium iodide (15.38 g, 67.6% yield) m.p. 212°-213° C., microanalysis, found: C,45.6; H,5.1; N,15.4%; $C_{14}H_{19}NI$ requires: C,45.52; H,5.17; N,15.13%; NMR: 2.2-2.4(3H,s,CH$_3$), 2.85-3.15 (3H,br,NHCH$_3$), 3.4(3H,s,N$_4$-CH$_3$), 3.5-(3H,s,N-CH$_3$), 5.7-5.85 (1H,br,pyrimidine 5-H), 7.35-7.6(5H, complex, aromatic), 8.1-8.25(1H,br,NH).

[Note: the site of quaternisation was confirmed by conventional Nuclear Overhauser studies].

The pyrimidine starting material was prepared as follows:

A mixture of 4-chloro-6-methyl-2-methylaminopyrimidine (21.0 g, 133 mM; described in UK Patent Specification Ser. No. 152327) and N-methylaniline (15.69 g, 147 mM) was heated as a melt at 95°-100° C. for 15 hours. The residue was partitioned between methylene chloride (200 mL) and 2M hydrochloric acid (200 ml) and then stirred for 15 minutes. The organic phase was separated and the aqueous phase was extracted again with further portions of methylene chloride (2×25 ml). This procedure was repeated and the combined organic layers were dried (MgSO$_4$) and the solvent evaporated. The residual solid was recrystallised from hexane to give 6-methyl-2-methylamino-4-N-methylanilinopyrimidine (21.8 g, 72% yield), m.p. 114°-114.5° C.; microanalysis, found: C,68.2; H,7.1; N,24.7%; $C_{13}H_{16}N_4$ requires C,68.39; H,7.06; N,24.54%.

EXAMPLES 21-46

The procedure described in Example 20 was repeated using the appropriate substituted pyrimidine of formula III and alkylating agent of formula $R^1.Y$. There were thus obtained the following compounds of formula I ($R^1=R^6=CH_3$, $R^5=H$; $Y^-=$iodide):

| Ex | $R^2$ | $R^4$ | Q.A | recrystallisation solvent(s) | melting point (°C.) | yield (%) |
| --- | --- | --- | --- | --- | --- | --- |
| 21 | NHCH$_3$ | Et | phenyl | EtOAc/EtOH | 158-160 | 58 |
| 22 | NHCH$_3$ | Pr | phenyl | EtOAc/Me$_2$CO | 166-167 | 52 |
| 23 | NHCH$_3$ | Pr$^i$ | phenyl | Me$_2$CO | 217-219 | 59 |
| 24 | NHCH$_3$ | allyl | phenyl | EtOAc/EtOH | 152-153 | 50 |
| 25 | NHCH$_3$ | Bu | phenyl | EtOAc | 160.5-161.5 | 48 |
| 26 | NHCH$_3$ | pentyl | phenyl | EtOAc/EtOH | 160-162 | 51 |
| 27 | NHCH$_3$ | H | phenyl | EtOH | 292-293 | 55 |
| 28 | NHCH$_3$ | Me | 4-chlorophenyl | Pr$^i$OH | 206-208 | 68 |
| 29 | NHCH$_3$ | Me | 4-methylphenyl | Pr$^i$OH | 205-206 | 44 |

-continued

| Ex | $R^2$ | $R^4$ | Q.A | recrystallisation solvent(s) | melting point (°C.) | yield (%) |
|---|---|---|---|---|---|---|
| 30 | $NHCH_3$ | allyl | 2,5-dimethyl-phenyl | EtOAc/EtOH | 142–145 | 60 |
| 31 | $NHCH_3$ | pentyl | 2,5-dimethyl-phenyl | EtOAc | 177–178 | 43 |
| 32 | $NH_2$ | Me | phenyl | $Pr^iOH$ | 250–251.5 | 49 |
| 33 | $NH_2$ | H | 2-nitrophenyl | EtOH/$H_2O$ | 265–267 | 36 |
| 34 | $NH_2$ | H | 4-chlorophenyl | EtOH/$H_2O$ | 278–280 | 7 |
| 35 | $NH_2$ | H | 2-carboxy-phenyl** | $H_2O$ | 185–186 | 38 |
| 36 | $NH_2$ | H | 3,5-dimethyl-phenyl | EtOH | 265–266 | 46 |
| 37 | $NH_2$ | H | 3,5-dichloro-phenyl | EtOAc/EtOH | 310–311* | 26 |
| 38 | $NH_2$ | H | 3,5-dibromo-phenyl | EtOH | 276–278 | 33 |
| 39 | $NH_2$ | Me | 2,5-dimethyl-phenyl | dioxan | 236–237 | 21 |
| 40 | $NH_2$ | Me | 3,5-dimethoxy-phenyl | EtOAc/EtOH | 276–277 | 56 |
| 41 | $NMe_2$ | H | phenyl | EtOH | 220–222 | 46 |
| 42 | $NMe_2$ | H | 2,5-dimethyl-phenyl | EtOH | 230–231* | 28 |
| 43 | $NMe_2$ | H | 3,5-dimethyl-phenyl | EtOH | 237–238 | 48 |
| 44 | $NMe_2$ | H | phenyl | $Pr^iOH$ | 133–133 | 32 |

** isolated as the p-toluenesulphonate salt.
* melting point accompanied by decomposition.

EXAMPLE 45

Similarly, 1,6-dimethyl-4-(1,2,3,4-tetrahydro-1-quinolylamino)-2-methylaminopyrimidinium iodide was obtained as a solid in 28% yield, m.p. 128°–130° C., by reaction of 6-methyl-4-(1,2,3,4-tetrahydro-1-quinolylamino)-2-methylaminopyrimidine with methyl iodide.

The necessary starting pyrimidines of formula III ($R^6=CH_3$, $R^5=H$) were made in an analogous manner to that described for the starting material of Example 20 and had the following properties:

| III No. | $R^2$ | $R^4$ | Q.A | Recrystallisation Solvent(s) | Melting Point (°C.) | Yield (%) |
|---|---|---|---|---|---|---|
| 1 | NHMe | Et | phenyl | hexane | 125–127 | 62 |
| 2 | NHMe | Pr | phenyl | cyclohexane | 140–141 | 43 |
| 3 | NHMe | $Pr^i$ | phenyl | EtOAc | 151–152 | 34 |
| 4 | NHMe | allyl | phenyl | — | 114–116 | 61 |
| 5 | NHMe | Bu | phenyl | hexane | 102–104 | 21 |
| 6 | NHMe | pentyl | phenyl | — | 85–87 | 47 |
| 7 | NHMe | H | phenyl | EtOAc | 135–136 | 61 |
| 8 | NHMe | Me | 4-chlorophenyl | hexane | 127–129 | 35 |
| 9 | NHMe | Me | 4-methylphenyl | hexane | 128–129 | 49 |
| 10 | NHMe | allyl | 2,5-dimethyl-phenyl | $Et_2O$ | 95–97 | 53 |
| 11 | NHMe | pentyl | 2,5-dimethyl-phenyl | $Et_2O$/pentane | 97–99 | 39 |
| 12 | $NH_2$ | Me | phenyl | hexane/EtOAc | 149–150 | 35 |
| 13 | $NH_2$ | H | 2-nitrophenyl | butanol | 188–189 | 50 |
| 14 | $NH_2$ | H | 4-chlorophenyl | butanol | 214–217 | 30 |
| 15 | $NH_2$ | H | 2-carboxy-phenyl | $H_2O$ | 303 + (decomp.) | 60 |
| 16 | $NH_2$ | H | 3,5-dimethyl-phenyl | EtOAc/hexane | 171–173 | 63 |
| 17 | $NH_2$ | H | 3,5-dichloro-phenyl | acetonitrile | 175–176 | 61 |
| 18 | $NH_2$ | H | 3,5-dibromo-phenyl | acetonitrile | 179–181 | 43 |
| 19 | $NH_2$ | Me | 2,5-dimethyl-phenyl | ethanol | 179–181* | 21 |
| 20 | $NH_2$ | H | 3,5-dimethoxy-phenyl | EtOAc/hexane | 149–150 | 31 |
| 21 | $NMe_2$ | H | phenyl | hexane/EtOAc | 134–135 | 35 |
| 22 | $NMe_2$ | H | 2,5-dimethyl-phenyl | pentane | 110–11 | 48 |
| 23 | $NMe_2$ | H | 3,5-dimethyl-phenyl | hexane | 80–81 | 34 |
| 24 | $NMe_2$ | Me | phenyl | $Et_2O$ ** | 166–167 | 78 |

* isolated as fumarate salt
** isolated as dibenzoyl tartrate salt

Similarly the starting material for Example 45, that is 6-methyl-4-(1,2,3,4-tetrahydro-1-quinolylamino)-2-methylaminopyrimidine, was obtained as a solid in 41% yield, m.p. 215°-216° C. (hydrochloride salt), by reaction of 4-chloro-6-methyl-2-methylaminopyrimidine with 1,2,3,4-tetrahydroquinoline.

EXAMPLE 46

Using an analogous procedure to that described in Example 1, was repeated but starting from the known compound 1,6-dimethyl-2-methylaminopyrimidin-4-one (Agai e.t. alia, Period. *Polytech. Chem. Eng.*, 1974, 18, 47) which was then reacted with phosphorus oxychloride to produce the corresponding reactive quaternary derivative, there was obtained 1,6-dimethyl-2-methylamino-4-(N-methyl-3-phenoxypropylamino)-pyrimidinium chloride, as a solid, m.p. 167°-169° C. (recrystallised from acetone/water) in 22% yield (partial hydrate: 0.25 $H_2O$).

EXAMPLES 47-49

A mixture of 2-amino-4-chloro-1,6-dimethylpyrimidinium iodide (1.43 g, 5 mM), N-allylaniline (0.67 g, 5 mM), dioxan (15 ml) and N,N-dimethylformamide (15 ml) was heated at 90°-100° C. for 15 hours. The volatile material was removed by evaporation and the residue was crystallised from ethanol to give 4-N-allylanilino-2-amino-1,6dimethylpyrimidinium iodide, (Example 47), (0.35 g, 15% yield), m.p. 271°-272° C.; microanalysis, found: C,46.8; H,5.0; N,14.9; $C_{15}H_{19}N_4I$ requires: C,47.1; H,4.97; N,14.66; NMR (200 MHz): 2.3(3H,s,C.$CH_3$), 3.45(3H,s,N.$CH_3$), 4.5-4.6(2H,d,N$CH_2$), 5.1-5.25(2H, s+d, CH=$CH_2$), 5.65-5.8(1H, br, pyrimidine 5$\overline{H}$), 5.8-6.0(1H,m,$\overline{CH}$=$CH_2$), 7.3-7.6(5H, complex, aromatic), 8.0-8.4($\overline{2H}$,br,$NH_2$).

[Note: the starting aminochloropyrimidine may is described by Ainley e.t. alia in *J. Chem. Soc.*, 1953, 59-70].

Using a similar procedure the following compounds of formula I were obtained:

(Example 48): 2-amino-4-N-ethylanilino-1,6-dimethylpyrimidinium iodide, as a solid in 25% yield, m.p. 231°-232° C. (recrystallised from 2-propanol), using N-ethylaniline instead of N-allylaniline; and (Example 49): 2-amino-4-(p-methylthioanilino)-1,6-dimethylpyrimidinium iodide, as a solid in 51% yield, m.p. 260°-262° C. (recrystallised from water) using p-methylthioaniline instead of N-allylaniline.

EXAMPLE 50

Using a similar procedure to that described in Example 20, 1,6-dimethyl-4-(1-indolyl)-2-methylaminopyrimidinium iodide was obtained as a solid in 33% yield, m.p. 304°-305° C., by reaction of 4-(1-indolyl)-6-methyl-2-methylaminopyrimidine with methyl iodide. The starting material was prepared as follows:

A mixture of 4-(1-indolinyl)-6-methyl-2-methylaminopyrimidine (2.4 g, 0.01M), 30% w/w palladium on charcoal (0.24 g) and diphenyl ether (10 ml) was heated under reflux in an argon atmosphere for 1 hour. The catalyst was then removed by filtration. The filtrate was then diluted with a large volume of hexane (100 ml). This gave a pale yellow solid which was recrystallised from 2-propanol to give 4-(1-indolyl)-6-methyl-2-methylaminopyrimidine (1.47 g, 62%), m.p. 160°-162° C.; microanalysis, found: C,70.5; H,5.9; N,23.6%; $C_{14}H_{14}N_4$ requires C,70.6; H,5.9; N,23.5%.

The 4-(1-indolinyl)-6-methyl-2-methylaminopyrimidine was obtained in 45% yield as its hydrochloride salt, m.p. >300° C. using a similar procedure to that described for the analogous intermediate in Example 20 but by reacting 4-chloro-6-methyl-2methylaminopyrimidine with indoline.

EXAMPLE 51

A mixture of 2-methyl-6-methylamino-4-N-ethylanilinopyrimidine (0.7 g, 2.9 mM), methyl iodide (0.54 ml, 8.7 mM) and dioxan (20 ml) was heated at reflux for 15 hours. The mixture was cooled. The solvent was removed in vacuo and the residual syrup was crystallised by addition of acetone. The solid was collected by filtration, washed with acetone and then recrystallised from ethyl acetate to give 1,2-dimethyl-6-methylamino-4-N-ethylanilinopyridinium iodide (0.55 g, 50% yield), m.p. 175°-177° C.; microanalysis, found: C,46.8; H,5.6; N,14.3%; $C_{15}H_{21}N_5I$ requires: C,46.88; H,5.5; N,14.58%; NMR: 1.1-1.2(3H,t,$CH_2CH_3$), 2.6(3H,s,$CH_3$), 2.6-2.7(3H,d,NH$CH_3$) 3.5(3H,s,N-$\overline{CH}_3$), 3.9-4.1(2H,q,$CH_2CH_3$), 5.15(1$\overline{H,s}$,pyrimidine 5-$\underline{H}$), 7.3-7.65(5H, complex, aromatic), 7.8-7.95(1H,br,N$\overline{H}$).

[Note: the site of quaternisation was confirmed by conventional Nuclear Overhauser studies].

The pyrimidine starting material was prepared as follows:

A mixture of 4-chloro-2-methyl-6-methylaminopyrimidine (2.0 g, 12.7 mM) and N-ethylaniline (3.06 g, 25.4 mM) was heated as a melt at 160° C. for 3 hours. The residue was cooled and acetone (10 ml) added. The resultant solid was collected by filtration and washed with acetone. There was thus obtained 2-methyl-6-methylamino-4-N-ethylanilinopyrimidine (2.25 g) as the hydrochloric salt. This salt (2.25 g, 7.9 mM) was dissolved in 2-propanol (50 ml) and a solution of potassium hydroxide (0.44 g, 7.9 mM) dissolved in the minimum volume of water was added. The mixture was heated at 90° C. for 5 minutes. The solvent was removed in vacuo. The resultant solid was stirred with water (25 ml) and then collected by filtration, washed with water and then dried at 100° C. to give 2-methyl-6-methylamino-4-N-ethylanilinopyrimidine (1.4 g, 46% yield), m.p. 144°-145° C.; microanalysis, found: C,69.1; H,7.5; N,22.8%; $C_{14}H_{18}N_4$ requires C,69.4; H,7.5; N,23.1%.

EXAMPLES 52-54

The procedure described in Example 51 was repeated using the appropriate substituted pyrimidine of formula III and alkylating agent of formula $R^1.Y$. There were thus obtained the following compounds of formula I (A=direct bond, $R^1=R^2=CH_3, R^5=H$; $Y^-$ =iodide):-

(Example 52): 1,2-dimethyl-6-amino-4-N-ethylanilinopyrimidinium iodide, as a solid, m.p. 195°-196° C. (recrystallised from ethyl acetate) in 65% yield;

(Example 53): 1,2-dimethyl-6-methylamino-4-N-methylanilinopyrimidinium iodide, as a solid, m.p. 198°-200° C. (recrystallised from 2-propanol) in 50% yield; and (Example 54): 1,2-dimethyl-6-ethylamino-4-N-methylanilinopyrimidinium iodide, as a solid, m.p. 212°-213° C. (recrystallised from acetone) in 49% yield.

The necessary starting materials were made in an analogous manner to that described for the starting material of Example 51 and had the following properties:

a) 6-amino-2-methyl-4-N-ethylanilinopyrimidine, as a solid, m.p. 126°–127° C. (triturated with ether) in 71% yield;

b) 2-methyl-6-methylamino-4-N-methylanilinopyrimidine, as a solid, m.p. 123°–124° C. (triturated with ether) in 60% yield; and c) 6-ethylamino-2-methyl-4-N-methylanilinopyrimidine, as a solid, m.p. 87°–89° C. (triturated with methylene chloride) in 80% yield.

EXAMPLE 55

Using a similar procedure to that described in Example 51, 1,2-dimethyl-4-(1-indolyl)-6-aminopyrimidinium iodide was obtained as a crystalline solid in 27% yield, m.p. 286° C. (with decomposition), (after recrystallisation from methanol), by reaction of 6-amino-4-(1-indolyl)-2-methylpyrimidine with methyl iodide.

The starting material was prepared as follows:

A mixture of 6-amino-4-(1-indolinyl)-2-methylpyrimidine (4.5 g, 20 mM), 30% w/w palladium on charcoal (0.45 g) and diphenyl ether (15 ml) was heated under reflux in an argon atmosphere for 1 hour. The solid was removed by filtration and the filtrate was diluted with hexane (100 ml) to give 6-amino-4-(1-indolyl)-2-methylpyrimidine (4.25 g, 95%) as a pale yellow solid, m.p. 176°–177° C.; microanalysis, found: C,69.5; H,5.5; N,24.4%; $C_{13}H_{12}N_4$ requires C,69.64; H,5.36; N,25.0%.

The 6-amino-4-(1-indolinyl)-2-methylpyrimidine was obtained as a solid, m.p. 209°–210° C., in a similar number to that described for the analogous intermediate in Example 51 by reaction of 6-amino-4-chloro-2-methylpyrimidine with indoline.

EXAMPLE 56

A column of quaternary ammonium hydroxide anion exchange resin was prepared from Amberlite* IRA400 (chloride form) by eluting the resin with sodium hydroxide (1M solution) until the eluate was free of chloride ions and then washing with deionised water (until the eluate was pH=7) and then with 10% v/v ethanol/water (500 ml). A mixture of 1,2-dimethyl-6-methylamino-4-N-ethylanilinopyrimidinium iodide (10.0 g) and 10% v/v ethanol/water (200 ml) was then loaded onto the column (approximate resin volume 100 ml). The column was eluted with 10% v/v ethanol/water (1l). The white solid which crystallised from the eluate was collected by filtration and recrystallised from ethanol/water to give 1,2-dimethyl-6-methylimino-4-N-ethylanilinopyrimidine (0.93 g), m.p. 82°–83° C.; microanalysis, found: C, 70.1; H, 7.8; N, 21.9%; $C_{15}H_{20}N_4$ requires: C, 70.3; H, 7.84; N, 21.86; NMR (200 MHz, DMSOd$_6$): 1.09(3H,t,-CH$_2$CH$_3$); 2.38(3H,s,pyrimidine-2-CH$_3$); 2.53(3H,s,=N-CH$_3$); 3.36(3H,s, pyrimidine N(1)-CH$_3$); 3.88(2H,q,—CH$_2$CH$_3$); 4.78(1H,s, pyrimidine 5-H); 7.22–7.34(3H, complex, aromatic), 7.40–7.50(2H, complex, aromatic).

[* Amberlite is a trade mark, the property of the Rohm and Haas Co.]

The filtrate was distilled under reduced pressure to reduce the volume to about 400 ml. The pH of the solution was adjusted, carefully to 6.65 by addition of M-hydrochloric acid. The mixture was then evaporated to dryness and triturated with ethyl acetate. The white crystalline solid was recrystallised from a mixture of ethyl acetate and 2-propanol to give 1,2-dimethyl-6-methylamino-4-N-ethylanilinopyrimidinium chloride (4.69 g), m.p. 201.5°–202.5° C., microanalysis, found C, 61.2;H, 7.3;N, 19.1%; $C_{15}H_{21}N_4Cl$ requires: C, 61.5;H, 7.2;N, 19.1%; NMR (200 MHz, DMSOd$_6$): 1.14(3H,t,—CH$_2$CH$_3$); 2.61(3H,s,pyrimidine-2-CH$_3$); 2.63(3H,s,NHCH$_3$); 3.65 (3H,s, pyrimidine-N(1)-CH$_3$); 4.01(2H,q,—CH$_2$—CH$_3$); 5.13 (1H,s,pyrimidine-5-H); 7.32–7.61(5H, complex, aromatic), 8.87 (1H,s,NH).

EXAMPLES 57–76

Using a similar procedure to that described in Example 20, the following compounds of formula I ($R^1=R^6=CH_3$, $R^5=H$; $Y^-$ =iodide) were obtained:

| Example | $R^2$ | $R^4$ | Q.A | Recryst. Solvent(s) | M.P. (°C.) | Yield (%) |
|---|---|---|---|---|---|---|
| 57 | NHMe | Et | 4-methylphenyl | MeOH/EtOAc | 196–199 | 88 |
| 58 | NH.crotyl | H | phenyl | MeOH/EtOAc | 220–221 | 14 |
| 59 | NHMe | 2-butynyl | phenyl | Pr$^i$OH | 191–183 | 47 |
| 60 | NH$_2$ | 2-propynyl | phenyl | Pr$^i$OH | 232–234 (dec.) | 62 |
| 61 | NHEt | Et | phenyl | Pr$^i$OH | 172–173 | 39 |
| 62 | NHEt | Me | phenyl | Pr$^i$OH | 183–184 | 39 |
| 63 | NHEt | allyl | phenyl | EtOAc | 104–106 | 46 |
| 64 | NHPr$^i$ | Me | phenyl | Pr$^i$OH/Et$_2$O | 165–166 | 37 |
| 65 | NHBu | Me | phenyl | Me$_2$CO/Et$_2$O+ | 146–147 | 40 |

Note
crotyl is equivalent to 2-butenyl
+ triturated with solvent

The following compounds of formula I ($R^6=CH_3$, $R^5=H$, Q.A-phenyl; $Y^-$ =iodide) were obtained in a similar manner:

| Example | $R^1$ | $R^2$ | $R^4$ | Recryst. Solvent(s) | M.P. (°C.) | Yield (%) |
|---|---|---|---|---|---|---|
| 66 | Et | NH$_2$ | H | H$_2$O | 263–265 (dec.) | 63 |
| 67 | Et | NH$_2$ | Me | Pr$^i$OH | 213–214 | 39 |
| 68 | Pr | NH$_2$ | Me | Me$_2$CO | 199–202 | 13 |
| 69 | Et | NHMe | Et | Pr$^i$OH | 146–148 (dec.) | 58 |
| 70 | Et | NH$_2$ | Et | Pr$^i$OH | 223–224 | 39 |

-continued

| Example | R$^1$ | R$^2$ | R$^4$ | Recryst. Solvent(s) | M.P. (°C.) | Yield (%) |
|---------|------|-------|------|---------------------|------------|-----------|
| 71 | Pr | NH$_2$ | Et | cyclohexane | 184–188 | 31 |
| 72 | allyl | NH$_2$ | Et | Pr$^i$OH | 202–203 | 35 |
| 73 | Me | piperidino | Et | CH$_2$Cl$_2$+ | 160–162 | 17 |

+ triturated with solvent (Example 74): 2-amino-1-ethyl-4-(3,5-dimethylanilino)-6-methylpyrimidinium iodide was similarly obtained as a solid in 28% yield, m.p. 226°–227° C., by reaction of 2-amino-4-(3,5-dimethylanilino)-6methylpyrimidine with ethyl iodide;

(Example 75): 2-amino-1,6-dimethyl-4-(2-methyl-1,2,3,4-tetrahydro-1-quinolylamino)pyrimidinium iodide was similarly obtained as a solid in 32% yield, m.p. 216°–218° C., by reaction of 2-amino-6-methyl-4-(2-methyl-1,2,3,4-tetrahydro-1-quinolylamino)pyrimidine with methyl iodide; and (Example 76): 2-amino-1,6-dimethyl-4-(2,4-dimethyl-1,2,3,4-tetrahydro-1-quinolylamino)pyridinium iodide was similarly obtained as a solid in 8% yield, m.p. 140°–142° C., by reaction of 2-amino-6-methyl-4-(2,4-dimethyl-1,2,3,4-tetrahydro-1-quinolylamino)pyrimidine with methyl iodide.

The necessary starting pyrimidines of formula III (R$^6$=CH$_3$, R$^5$=H) were obtained in an analogous manner to that described for the starting material of Example 20 and had the following properties: [Note: the starting material for Example 60 was made by alkylation of a solution of the starting material for Example 66 in DMF with propargyl bromide using sodium hydride as base.]

and the solvent evaporated to give 2-butylamino-4-chloro-6-methylpyrimidine (8.1 g) as a solid, m.p. 35°–36° C., in 88% yield.

The starting 4-anilino-2-crotylamino-6-methylpyrimidine required to prepare the compound III for Example 58 was prepared as follows:

A mixture of 2-amino-4-anilino-6-methylpyrimidine (1 g) (5 mM), potassium carbonate (0.4 g, 5.5 mM), crotyl bromide (0.61 ml) (5 mM) and acetone (25 ml) was heated at reflux for 20 hours. The solvent was then evaporated and the residue triturated with methylene chloride. The methylene chloride extracts were combined and the solvent removed by evaporation. The residual syrup was purified by flash chromatography using Merck 9835 silica (200 g) and eluting with 5% v/v methanol/methylene chloride. There thus was obtained 4-anilino-2-crotylamino-6-methylpyrimidine as a viscous oil (0.36 g) which was used without characterisation.

The starting 2-amino-6-methyl-4-(2-methyl-1,2,3,4-tetrahydro-1-quinolylamino)pyrimidine for Example 75 was obtained as a solid in 32% yield, m.p. 140°–142° C., by reaction of 4-chloro-6-methyl-2-methylaminopyrimidine with 2-methyl-1,2,3,4-tetrahydroquinoline. Similarly, the starting 2-amino-6-methyl-4-(2,4-dimethyl-

| III for Ex. no. | R$^2$ | R$^4$ | Q.A | Recryst. Solvent(s) | M.P. (°C.) | Yield (%) |
|-----------------|-------|-------|-----|---------------------|------------|-----------|
| 57 | NHMe | Et | 4-methylphenyl | Note (a) | 138–140 | 44 |
| 58 | NH.crotyl | H | phenyl | Note (a) | oil | 28 |
| 59 | NHMe | 2-butynyl | phenyl | EtOAc | 141–143 | 57 |
| 60 | NH$_2$ | —CH$_2$—C≡CH | phenyl | cyclohexane | 106–108 | 50 |
| 61 | NHEt | Et | phenyl | Note (a) | 91–93 | 76 |
| 62 | NHEt | Me | phenyl | hexane | 89–90 | 37 |
| 63 | NHEt | allyl | phenyl | Pr$^i$OH | 112–113 | 61 |
| 64 | NHPr | Me | phenyl | Et$_2$O | 77–79 | 85 |
| 65 | NHBu | Me | phenyl | Note (a) | 146–147 | 54 |
| 66 | NH$_2$ | H | phenyl | EtoAc | 161–163 | 48 |
| 67,68 | NH$_2$ | Me | phenyl | hexane/EtOAc | 148–150 | 35 |
| 69 | NHMe | Et | phenyl | hexane | 125–127 | 62 |
| 70–72 | NH$_2$ | Et | phenyl | Note (a) | 113–114 | 64 |
| 73 | piperidino | Et | phenyl | — | oil | 99 |
| 74 | NH$_2$ | H | 3,5-Me$_2$-phenyl | EtOAc/hexane | 171–173 | 63 |

Notes
crotyl is equivalent to 2-butenyl
(a): purified by chromatography on silica using ethyl acetate/hexane as eluant.

The starting 2-butylamino-4-chloro-6-methylpyrimidine needed to prepare the compound III for Example 65 was prepared as follows:

2-Butylamino-6-methylpyrimidin-4-one (8.4 g, 0.046M) was treated with phosphorus oxychloride (5 ml). A vigorous reaction ensued. When this had subsided, the resultant mixture was heated at 90° C. for 30 minutes. This gave an orange coloured syrup which was cooled and added to water to decompose the excess phosphorus oxychloride. The aqueous solution was adjusted to pH 7 using 2M sodium hydroxide solution. The resultant white precipitate was extracted with methylene chloride. The extracts were dried (MgSO$_4$)

1,2,3,4-tetrahydro-1-quinolylamino)pyrimidine for Example 76, was obtained as a solid in 44% yield, m.p. 144°–146° C., by reaction of 4-chloro-6-methyl-2-methylaminopyrimidine with the known compound 2,4-dimethyl-1,2,3,4-tetrahydroquinoline (Chemical Abstracts Registry No. 67525-06-8).

EXAMPLES 77–102

The procedure described in Example 20 was repeated using the appropriate substituted pyrimidine of formula III and alkylating agent of formula R$^1$.I. There were thus obtained the following compounds of formula I (Q.A=phenyl, R⁵=H, Y⁻=iodide):

| Example | R¹ | R² | R⁴ | R⁶ | Recrystallisation solvent(s) | M.P. (°C.) | yield (%) |
|---|---|---|---|---|---|---|---|
| 77 | Me | NH₂ | Me | Et | MeOH/Et₂O | 226-230- | 64 |
| 78 | Me | NH₂ | Me | Pr | dioxan | 206-210* | 62 |
| 79 | Me | NH₂ | Me | Bu | Pr^iOH/Et₂O | 173-174 | 62 |
| 80 | Me | NH₂ | Me | Bu^i | Pr^iOH/Et₂O | 167-168 | 48 |
| 81 | Me | NH₂ | Me | PhCH₂CH₂ | Pr^iOH/Et₂O | 175-180 | 44 |
| 82 | Me | NH₂ | Me | 3-butenyl | Pr^iOH/Et₂O | 148-150 | 53 |
| 83 | Et | NH₂ | Me | Et | MeOH/Et₂O | 194-196* | 23 |
| 84 | Et | NH₂ | Me | Pr | MeOH/Et₂O | 199-201* | 18 |
| 85 | Me | NHMe | Me | Et | MeOH/Et₂O | 208-210* | 26 |
| 86 | Me | NH₂ | Et | Et | MeOH/Et₂O | 236-238* | 16 |
| 87 | Me | NH₂ | Et | Pr | MeOH/Et₂O | 198-200* | 59 |
| 88 | Me | NH₂ | Et | Bu | Pr^iOH/Et₂O | 147-148 | 35 |
| 89 | Me | NH₂ | Et | pentyl | Pr^iOH/Et₂O | 164-166 | 66 |
| 90 | Me | NH₂ | Et | 3-butenyl | Pr^iOH/Et₂O | 133-134 | 39 |
| 91 | Me | NH₂ | Et | EtOCH₂ | Pr^iOH/Et₂O | 208-212 | 74 |
| 92 | Me | NHMe | Et | Et | MeOH/Et₂O | 158-160 | 35 |
| 93 | Me | NHMe | Et | Pr | MeOH/Et₂O | 143-145 | 31 |
| 94 | Et | NH₂ | Et | Et | MeOH/Et₂O | 190-192* | 38 |
| 95 | Et | NH₂ | Et | Pr | MeOH/Et₂O | 196-198* | 51 |
| 96 | Me | NHEt | Me | Et | MeOH/Et₂O | 183-186+ | 48 |
| 97 | Me | NHEt | Me | Pr | MeOH/Et₂O | 168-170+ | 39 |
| 98 | Me | NHEt | Et | Et | MeOH/Et₂O | 160-163* | 44 |
| 99 | Me | NHEt | Et | CH₂OEt | Pr^iOH/Et₂O | 130-131 | 58 |
| 100 | Et | NHEt | Et | Et | MeOH/Et₂O | 165-167 | 29 |

Notes
*Melting point accompanied by decomposition
+ obtained as a partial methanolate (0.5 MeOH)

The necessary starting pyrimidines of formula III (Q.A=phenyl, R⁵=H) were made in an analogous manner to that described for the starting material of Example 20 and had the following properties:

| III for Ex. No. | R² | R⁴ | R⁶ | Recryst. Solvent(s) | M.P. (°C.) | Yield (%) |
|---|---|---|---|---|---|---|
| 77,83 | NH₂ | Me | Et | Et₂O | 105-106 | 14 |
| 78,84 | NH₂ | Me | Pr | Et₂O/hexane | 104-106 | 24 |
| 79 | NH₂ | Me | Bu | hexane | 66-67 | 65 |
| 80 | NH₂ | Me | Bu^i | hexane | 107-109 | 78 |
| 81 | NH₂ | Me | PhCH₂CH₂ | Et₂O/hexane | 110-111 | 55 |
| 82 | NH₂ | Me | 3-butenyl | hexane | 46-48 | 46 |
| 85 | NHMe | Me | Et | + | 84-88 | 17 |
| 86 | NH₂ | Et | Et | + | 115-117 | 87 |
| 87 | NH₂ | Et | Pr | + | 93-95 | 64 |
| 88 | NH₂ | Et | Bu | hexane | 87-88 | 44 |
| 89 | NH₂ | Et | pentyl | hexane | 102-103 | 86 |
| 90 | NH₂ | Et | 3-butenyl | hexane | 79-81 | 46 |
| 91 | NH₂ | Et | EtOCH₂ | + | 126-128 | 32 |
| 92 | NHCH₃ | Et | Et | + | 118-122 | 11 |
| 93 | NHCH₃ | Et | Pr | + | 80-82 | 8 |
| 96 | NHEt | Me | Et | + | oil | 20 |
| 97 | NHEt | Me | Pr | + | oil | 44 |
| 98,100 | NHEt | Et | Et | + | 68-72 | 61 |
| 99 | NHEt | Et | EtOCH₂ | hexane | 50-51 | 55 |

+ purified by flash chromatography on silica using 0.5% v/v methanol in dichloromethane as eluant and used without further purification.

The following compounds of formula I were obtained in a similar manner:

(Example 101): 2-amino-4-(N-ethylanilino)-5,6,7,8-tetrahydro-1-methylquinazolinium iodide obtained as a partial hydrate (0.25 H₂O), m.p. 221°-223° C. (after recrystallisation from methanol/ether) in 48% yield by reaction of methyl iodide with 2-amino-(4-N-ethylanilino)-5,6,7,8-tetrahydroquinazoline; [the latter compound was itself obtained as a solid, m.p. 132°-134° C., in 11% yield by reaction of 2-amino-4-chloro-5,6,7,8-tetrahydroquinazoline with N-ethylaniline;].

(Example 102): 2-amino-4-(N-ethylanilino)-1-methylquinazolinium iodide was similarly obtained as a solid, m.p. 252°-254° C. (dec.) (recrystallised from methanol/ether) in 37% yield by reaction of methyl iodide with 2-amino-(4-N-ethylanilino)-quinazoline; [the latter compound was itself obtained as a solid, m.p. 168°-170° C., in 11% yield by reaction of 2-amino-4-chloroquinazoline with N-ethylaniline;]

Certain of the chloropyrimidines of formula IV (X=Cl, R⁵=H) which were used as starting materials in Examples 77-102 are known compounds, and are described in the following references:

(a) R⁶=H, R²=NH₂; *Tetrahedron*, 1968, 24, 3595;

(b) R⁶=Et, R²=NH₂; Belgian Patent no. 657, 135, Jan. 15, 1965; and (c) R⁶=CH₂CH₂Ph, R².NH₂; *J. Org. Chem.*, 27, 1717.

The method by which the other chloropyrimidines of formula IV (X=Cl, R⁵=H) were prepared is illustrated by the following preparation of 4-chloro-2-ethylamino-6-propylpyrimidine:

(a) Ethyl 3-oxo-hexanoate (4.74 g; 30 mM) and N-ethylguanidine sulphate (4.08 g; 30 mM) were dissolved in a solution prepared by dissolving sodium (1.4 g; 0.65 g atom) in ethanol (100 ml) and the mixture was heated under reflux on the steam bath for 18 hours. Acetic acid (5 ml) was added to the cooled mixture which was stirred for 10 minutes. Insoluble material was removed by filtration and the filtrate was evaporated. The residue was partitioned between water (50 ml) and methylene chloride (50 ml). The aqueous layer was extracted twice with methylene chloride (50 ml). The combined extracts were dried and the solvent evaporated. The residue was crystallised from cyclohexane to give 2-ethylamino-4-hydroxy-6-propylpyrimidine as a solid (4.6 g; 85% yield), m.p. 108°–110° C.

(b) A mixture of 2-ethylamino-4-hydroxy-6-propylpyrimidine (1.81 g, 10 mM) and phosphorus oxychloride (15 ml) was heated at 100° C. for 18 hours. The excess of phosphorus oxychloride was removed under reduced pressure and the residual was decomposed with ice-water (50 ml). The solution was made basic with concentrated aqueous ammonia and extracted with ethyl acetate (3×50 ml). The extracts were combined, dried and the solvent evaporated to give 4-chloro-2-ethylamino-6-propylpyrimidine (1.79 g; 90% yield) as an oil which was used without purification.

Other chloropyrimidines of formula IV (X=Cl, $R^5$=H) were obtained using a similar procedure from the corresponding hydroxypyrimidines of formula IV (X=OH, $R^5$=H). The latter compounds had the following properties:

| Number | $R^2$ | $R^6$ | Recryst. solvent(s) | M.P. (°C.) | Yield (%) |
| --- | --- | --- | --- | --- | --- |
| 1 | NH$_2$ | Bu | + | 212–216 | 85 |
| 2 | NH$_2$ | Bu$^i$ | + | 231–234 | 30 |
| 3 | NH$_2$ | 3-butenyl | + | 186–189 | 83 |
| 4 | NH$_2$ | pentyl | + | 188–191 | 79 |
| 5 | NH$_2$ | EtOCH$_2$ | + | 244–245 | 69 |
| 6 | NHMe | Et | EtOAc | 204–208 | 46 |
| 7 | NHMe | Pr | EtOAc | 190–192 | 54 |
| 8 | NHEt | Et | cyclohexane | 144–116 | 39 |
| 9 | NHEt | CH$_2$OEt | cyclohexane | 106–108 | 54 |

+ Triturated with ether and used without further purification

The majority of chloropyrimidines of formula IV (X=Cl, $R^5$=H) were used without characterisation, but the following were characterised:

| Number | $R^2$ | $R^6$ | Recryst. solvent(s) | M.P. (°C.) | Yield (%) |
| --- | --- | --- | --- | --- | --- |
| 1 | NH$_2$ | Bu | Et$_2$O/hexane | 58–59 | 50 |
| 2 | NH$_2$ | Bu$^i$ | Et$_2$O/hexane | 104–106 | 33 |
| 3 | NH$_2$ | pentyl | Et$_2$O/hexane | 58–59 | 29 |

The starting 2-amino-4-chloroquinazoline derivatives (from which the 2-amino-4-N-ethylanilino starting materials for Examples 101 and 102 were prepared) were obtained in an analogous manner to the above chloropyrimidines and were used without purification.

The starting 2-amino-4-hydroxyquinazoline derivatives were themselves obtainable as solids, m.p.>300° C. using literature procedures (for example 2-amino-5,6,7,8-tetrahydro-4-hydroxyquinazoline Chem. Pharm. Bull. (Japan), 1986, 34, 4150; 2-amino-4-hydroxyquinazoline: Rec. trav. chim. Pays. Bas., 1960, 79, 443).

EXAMPLES 103–109

Using a similar procedure to that described in Example 47, the following compounds of the formula 1 (as set out hereinafter) were obtained:

| Example | X | $R^4$ | Recryst. solvent(s) | M.P. (°C.) | Yield (%) |
| --- | --- | --- | --- | --- | --- |
| 103 | H | Pr | Me$_2$CO * | 250–255 | 25 |
| 104 | H | 2-butynyl | Me$_2$CO | 182–184 | 47 |
| 105 | H | Bu | Pr$^i$OH/Et$_2$O | 184–186 | 25 |
| 106 | 2-MeO | Et | Pr$^i$OH/Et$_2$O | 267–269 | 12 |
| 107 | 2-Me | Et | CH$_2$Cl$_2$ * | 216–217 | 22 |
| 108 | 4-Cl | Et | MeOH/Et$_2$O | 244–246 | 42 |
| 109 | 4-Me | Et | MeOH/Et$_2$O | 240–242 | 32 |

* triturated with solvent

EXAMPLES 110–112

Using an analogous procedure to that described in Example 20, but starting from the appropriate 4-(indol-1-yl)-6-methylpyrimidine of formula 2 (as set out hereinafter) and alkylating agent of formula $R^1.I$, the following compounds of the formula 3 (set out hereinafter; $R^6$=CH$_3$) were obtained:

| Example | $R^1$ | $R^2$ | X | B | Recryst. Solvent(s) | M.P. (°C.) | Yield (%) |
| --- | --- | --- | --- | --- | --- | --- | --- |
| 110 | Et | NHMe | H | H | Dioxan * | 294–295 | 6 |
| 111 | Me | NHMe | H | 2-Me | EtOH/H$_2$O | 301–302+ | 43 |
| 112 | Me | NHMe | 5-MeO | H | EtOH/H$_2$O | 304–305+ | 31 |
| 113 | Me | NH$_2$ | H | H | EtOH/Et$_2$O | 295–296 | 55 |
| 114 | Et | NH$_2$ | H | H | EtOH * | 284–286 | 7 |
| 115 | Me | NH$_2$ | 5-MeO | H | H$_2$O/EtOH | 297–298 | 47 |
| 116 | Me | NH$_2$ | H | 2-Me | EtOH/H$_2$O | 286–288 | 43 |
| 117 | Me | NH$_2$ | 5-Cl | H | EtOH/H$_2$O | 288–290 | 37 |
| 118 | Me | NH$_2$ | 5-CN | H | EtOH | 280–282 | 10 |
| 119 | Me | NH$_2$ | 5-Br | H | EtOH/H$_2$O | 295–296 | 41 |
| 120 | Me | NH$_2$ | 5-Me | H | EtOH/H$_2$O | 287–288 | 37 |
| 121 | Me | NH$_2$ | 7-aza | H | EtOH/H$_2$O | 285+ | 9 |
| 122 | Me | NH$_2$ | 5-F | H | MeOH | 279–281 | 15 |

+ with decomposition
* triturated with solvent

The indolyl starting materials for Examples 110 and 113 were prepared in a similar manner to Example 20 and Example 50 by dehydrogenating the appropriate 4-(indolin-1-yl)pyrimidine with 30% w/w palladium-on-charcoal heated under reflux with diphenyl ether in an argon atmosphere. The required starting 2-amino-4-(1-indolinyl)-6-methylpyrimidine was obtained as a solid, m.p. 242°-244° C. in 48% yield in a similar manner to that described for the analogous intermediate in Example 13 by reaction of 2-amino-4-chloro-6-methylpyrimidine with indoline.

The remaining indolyl starting materials of formula 2 were obtained by alkylation of the appropriate indole with the required chloropyrimidine in DMF using as base a 60% w/w dispersion of sodium hydride in mineral oil.

The following 4-(indol-1-yl)-6-methylpyrimidine derivatives of formula 2 ($R^6$=$CH_3$) were thus obtained:

| Cpd. 2 for Ex. | $R^2$ | X | B | Recryst. solvent(s) | m.p. (°C.) | yield (%) |
|---|---|---|---|---|---|---|
| 110 | NHMe | H | H | Pr$^i$OH | 160–162 | 62 |
| 111 | NHMe | H | 2-Me | cyclohexane | 163–165 | 54 |
| 112 | NHMe | 5-MeO | H | EtOAc | 188–189 | 47 |
| 113,114 | $NH_2$ | H | H | $CH_2Cl_2$* | 178–180 | 56 |
| 115 | $NH_2$ | 5-MeO | H | EtOH | 179–180 | 28 |
| 116 | $NH_2$ | H | 2-Me | EtOAc | 186–188 | 48 |
| 117 | $NH_2$ | 5-Cl | H | EtOAc | 193–195 | 42 |
| 118 | $NH_2$ | 5-CN | H | EtOAc | 210–212 | 56 |
| 119 | $NH_2$ | 5-Br | H | $Me_2CO$ | 194–196 | 21 |
| 120 | $NH_2$ | 5-Me | H | EtOAc | 186–188 | 33 |
| 121 | $NH_2$ | 7-aza | H | cyclohexane | 171–173 | 35 |
| 122 | $NH_2$ | 5-F | H | EtOAc | 198–200 | 38 |

* triturated with solvent

EXAMPLES 123–125

Using a similar procedure to that described in Example 20, the following compounds of formula I were obtained:

(Example 123): 1,6-dimethyl-4-(indolin-1-yl)-2-methylaminopyrimidinium iodide, as a solid, m.p. >300° C. (recrystallised from DMF), in 74% yield, starting from 4-(indolin-1-yl)-6-methyl-2-methylaminopyrimidine [described above in connection with Example 50];

(Example 124): 2-amino-1,6-dimethyl-4-(indolin-1-yl)pyrimidinium iodide, as a solid, m.p. 274–276 (recrystallised from ethanol), in 43%, starting from 2-amino-4-(indolin-1-yl)-6-methylpyrimidine, itself obtained in 64% yield as a solid, m.p. 157°–159° C. (recrystallised from cyclohexane), using a similar procedure to that for the analogous starting material in Example 50, but using 2-methylindoline instead of indoline; and (Example 125): 2-amino-1,6-dimethyl-4-(2,3-dimethylindolin-1-yl)pyrimidinium iodide, as a solid. m.p. 279°–281° C. (recrystallised from ethanol), in 55% yield, starting from 2-amino-6-methyl-4-(2,3-dimethylindolin-1-yl)pyrimidine, itself obtained in 50% yield as a solid, m.p. 179°–181° C. (recrystallised from ethyl acetate using a similar procedure to that for the analogous starting material in Example 50, but using 2,3-dimethylindoline instead of indoline.

EXAMPLES 126–130

Using a similar procedure to that described in Example 51, but starting with the appropriate substituted pyrimidine of formula III and methyl iodide, the following compounds of formula I (Q.A=phenyl; $R^1$=$R^2$=$CH_3$, $R^5$=H; Y⁻=iodide) were obtained:

| Example | $R^4$ | $R^6$ | Recryst. solvent(s) | M.P. (°C.) | Yield (%) |
|---|---|---|---|---|---|
| 126 | Me | $NH_2$ | 2-propanol | 228–230 | 86 |
| 127 | allyl | NHMe | EtOAc/MeOH | 68–71 | 59 |
| 128 | 2-butynyl | NHMe | EtOAc/MeOH | syrup | 15 |
| 129 | Pr | NHMe | EtOAc | 139–140 | 38 |
| 130 | Pr$^c$.$CH_2$ | NHMe | EtOAc | 147–149 | 47 |

Note:
Pr$^c$ = cyclopropyl

The necessary starting materials of formula III were made in an analogous manner to that described for the starting materials of Example 51 from the appropriate chloropyrimidines of formula IV (X=Cl) and had the following properties:

| III for Ex. no. | $R_4$ | $R_6$ | Recryst. solvent(s) | M.P. (°C.) | Yield (%) |
|---|---|---|---|---|---|
| 126 | Me | $NH_2$ | $CH_2Cl_2$ | 128–130 | 53 |
| 127 | allyl | NHMe | $Et_2O$ | 98–101 | 43 |
| 128 | 2-butynyl | NHMe | — | syrup | 45 |
| 129 | Pr$^n$ | NHMe | hexane | 114–114.5 | 53 |
| 130 | Pr$^c$.$CH_2$ | NHMe | hexane | 98–100 | 28 |

Note:
Pr$^c$ = cyclopropyl
*having a satisfactory NMR spectrum

EXAMPLES 131–135

The procedure described in Example 51 was repeated using the appropriate substituted pyrimidine of formula III and methyl iodide. There were thus obtained the following compounds of formula I (Q.A=phenyl, $R^1$=$CH_3$, $R^5$=H, $R^6$=$NHCH_3$; Y⁻=iodide):

| Example | $R_4$ | $R_2$ | Recryst. solvent(s) | M.P. (°C.) | Yield (%) |
|---|---|---|---|---|---|
| 131 | Me | Et | Pr$^i$OH/$Et_2O$ | 173–174 | 41 |
| 132 | Me | H | Pr$^i$OH/$Et_2O$ | 172–173 | 81 |
| 133 | Et | Et | EtOAc | 146–147 | 44 |
| 134 | Et | Pr | $Me_2CO$/$Et_2O$ | 127–130 | 27 |
| 135 | Et | Bu | MeOH/$Et_2O$ | 144–146 | 19 |

The necessary starting materials of formula III (Q.A=phenyl; $R^2$=$CH_3$, $R^5$=H) were made in an analogous manner to that described for the starting material of Example 51 from the appropriate chloropyrimidine of formula IV (X=Cl) and had the following properties:

| No. | $R^4$ | $R^2$ | Trituration solvent(s) | M.P. (°C.) | Yield (%) |
|---|---|---|---|---|---|
| 131 | Me | Et | $CH_2Cl_2$ | 98–100 | 71 |
| 132 | Et | H | Pr$^1$OH/$Et_2O$ | 113–114 | 44 |
| 133 | Et | Et | $CH_2Cl_2$ | 97–99 | 63.5 |
| 134 | Et | Pr | $CH_2Cl_2$ | 69–71 | 22 |
| 135 | Et | Bu | hexane | 75–75.5 | 31 |

The required chloropyridine starting materials of formula (IV) are themselves prepared by the addition of the appropriate 2-substituted-4,6-dichloropyrimidine to an alcoholic solution of the required amine with cooling below 10° C. The reaction mixture was then allowed to warm to ambient temperature and the solvent evaporated. The residue was partitioned between water and methylene chloride. The organic phase was dried ($MgSO_4$) and concentrated in vacuo to give the required compound of formula IV (X=Cl):

(a) 4-chloro-2-ethyl-6-methylaminopyrimidine, obtained as a solid, m.p. 80°–81° C.;

(b) 4-chloro-6-methylamino-2-propylpyrimidine, obtained as a solid, m.p. 30°–40° C.; and (c) 2-butyl-4-chloro-6-methylaminopyrimidine, obtained as an oil.

EXAMPLES 136-139

The procedure described in Example 51 was repeated using the appropriate substituted pyrimidine of formula III and alkylating agent of formula $R^1.Y$. There were thus obtained the following compounds of formula I ($R^4$=Et, $R^2$=CH$_3$, $R^5$=H, $R^6$=NHCH$_3$):

| | A = direct bond: | | | | |
|---|---|---|---|---|---|
| Example | Q.A- | $R^1$ | Y | Recryst. solvent(s) | m.p. (°C.) | yield (%) |
| 146 | p-tolyl | Me | I | MeOH/Et$_2$O | 188-191 | 31 |
| 147 | p-anisyl | Me | I | EtOH | 211-214 | 40 |
| 148 | p-Cl-phenyl | Me | I | MeOH/Et$_2$O | 243-245 | 60 |
| 149 | phenyl | Et | BF$_4$ | EtOAc* | 126-128 | 8 |

*triturated with solvent

The necessary starting materials of formula III were made in an analogous manner to that described for the starting material of Example 51, but using the appropriate N-ethylaniline:

a) 4-(N-ethyl-4-methylanilino)-2-methyl-6-methylaminopyrimidine obtained as a solid, m.p. 140°–143° C., in 70% yield;

(b) 4-(N-ethyl-4-methoxyanilino)-2-methyl-6-methylaminopyrimidine, obtained as a solid, m.p. 116°–118° C., in 71% yield; and (c) 4-(N-ethyl-4-chloroanilino)-2-methyl-6-methylaminopyrimidine, obtained as a solid, m.p. 133°–136°, in 79% yield.

[Note: the required starting material of formula III for Example 139 is described in Example 51].

EXAMPLES 140-144

Using a similar procedure to that described in Example 56, the following 1,2-dimethyl-6-methylamino-4-N-ethylanilinopyrimidium salts were obtained by reacting 1,2-dimethyl-6-methylimino-4-N-ethylanilinopyrimidine with the appropriate acid:

| Example | Salt | Recryst. solvent(s) | M.P. (°C.) | Yield (%) |
|---|---|---|---|---|
| 140 | fumarate | acetonitrile | 152-154 | 80 |
| 141 | benzoate | hexane* | 46-47 | 93 |
| 142 | hydrogen sulphate | Pr$^i$OH/Et$_2$O | 146-147 | 58 |
| 143 | acetate | hexane* | 43-45 | 62 |
| 144 | butyrate | Et$_2$O/hexane | 52-58 | 56 |

*triturated with solvent

EXAMPLES 145-154

Using a similar procedure to that described in Example 51, but starting from the appropriately substituted 4-(indol-1-yl)pyrimidine of formula 2 and methyl iodide, the following 4-(indol-1-yl)-1,2-dimethyl-6-methylaminopyrimidinium salts of the formula 3 ($R^1$=$R^2$=CH$_3$ and $R^6$=NHCH$_3$, except where stated) were obtained:

| Example | X | B | Recryst. solvent(s) | H.P. (°C.) | Yield (%) |
|---|---|---|---|---|---|
| 145 | H | H | MeOH | 270-272 (decomp.) | 14 |
| 146+ | H | 3-Me | MeOH | 276-277 | 7 |
| 147 | H | 3-Me | EtOH/H$_2$O | 257-258 | 24 |
| 148 | H | 3-Et | EtOH | 259-260 | 16 |
| 149* | H | 3-Et | EtOH | 249-250 | 24 |
| 150** | H | 3-Et | EtOH | 240-242 | 21 |
| 151 | H | 3-Pr | EtOH | 245-247 | 35 |
| 152 | H | 3-Ph | MeOH/H$_2$O | 254.5-255.5 | 20 |
| 153 | H | 3-Pr$^i$ | H$_2$O | 251-252 | 4 |
| 154 | 5-MeO | H | MeOH | 309-310 | 8 |

+$R_6$ = NH
*$R^2$ = Et
**$R_6$ = NHEt

The starting 4-(indol-1-yl)pyrimidines of formula 2 for Examples 145, 149 and 150 were obtained from the appropriate indoline and chloropyrimidine using a similar procedure to that used for the analogous starting material in Example 55.

The preparation of the starting 4-(indol-1-yl)pyrimidines of formula 2 for Examples 146, 147 and 151-154 is illustrated by the following preparation of the starting material for Example 148:

A mixture of 3-ethylindole (1.45 g, 10 mM), sodium hydride (60% w/w oil dispersion) (0.44 g, 11 mM) and dry DMF (10 ml) was stirred under an argon atmosphere. When effervescence had ceased, a mixture of 4-chloro-2-methyl-6-methylaminopyrimidine (1.575 g, 10 mM) and DMF (15 ml) was added. The mixture was stirred at 110° C. for 20 hours, cooled, water (10 ml) added and the solvent evaporated. The residue was dissolved in methylene chloride and purified by flash column chromatography on silica (Merck 9385) using ether as eluant to give 4-(3-ethyl-1-indolyl)-2-methyl-6-methylaminopyrimidine as a solid (0.64 g, 25%), m.p. 161°–162° C., (after recrystallisation from ethyl acetate); microanalysis, found: C,72.4; H,6.9; N,21.1%; C$_{16}$H$_{18}$N$_4$ requires C,72.18; H,6.77; N,21.05%.

The properties of the various starting materials of formula 2 for Examples 145-154 are summarised below:

| Cpd. 2 for Ex. | X | B | $R^2$ | $R^6$ | Recryst. solvent(s) | M.P. (°C.) | Yield (%) |
|---|---|---|---|---|---|---|---|
| 145 | H | H | Me | NHMe | Et$_2$O | 153-154 | 65 |
| 146 | H | Me | Me | NH$_2$ | EtOAc | 183-184 | 29 |
| 147 | H | Me | Me | NHMe | EtOAc/hexane | 156-157 | 32 |
| 148 | H | Et | Me | NHMe | EtOAc | 161-162 | 25 |
| 149 | H | Et | Et | NHMe | cyclohexane | 128-130 | 58 |
| 150 | H | Et | Me | NHEt | cyclohexane | 117-118 | 44 |
| 151 | H | Pr | Me | NHMe | EtOAc* | 144-146 | 31 |
| 152 | H | Ph | Me | NHMe | Et$_2$O | 151-152 | 35 |
| 153 | H | Pr$^i$ | Me | NHMe | hexane | 130-131 | 40 |
| 154 | 5-MeO | H | Me | NH$_2$ | EtOAC | 162-164 | 31 |

*triturated with solvent

The 4-(indolin-1-yl)-6-aminopyrimidines of the formula 4 (set out hereinafter) required for the formula 2 starting materials to Examples 145, 149 and 150, respectively, were obtained in a similar manner to that described for the analogous intermediate in Example 51 by reacting the appropriately substituted indoline with the required chloropyridine and had the following properties:

| No. | B | R$_2$ | R$^6$ | Recryst. solvent(s) | m.p. (°C.) | yield (%) |
|---|---|---|---|---|---|---|
| 1 | H | Me | NHMe | Ether/hexane | 174–177 | 93 |
| 2 | 3-Et | Et | NHMe | EtOAc | 168–170 | 32 |
| 3 | Et | Me | NHEt | MeCN | 146–148 | 17 |

EXAMPLES 155–158

Using a similar procedure to that described in Example 51, the following 1-indolinyl compounds of formula 5 (set out hereinafter) were obtained by reacting the appropriate indoline of formula 4 (R$^6$=NHCH$_3$) with methyl iodide:

| Example | B | R$^2$ | Recryst. solvent(s) | M.P. (°C.) | Yield (%) |
|---|---|---|---|---|---|
| 155 | H | Me | EtOH | 281–283+ | 50 |
| 156 | 3-Me | Me | EtOH | 261–262 | 51 |
| 157 | 3-Et | Et | Ether* | 240–241+ | 36 |
| 158 | 3-Et | Me | EtOH | 262–263 | 51 |

*triturated with solvent
+ with decomposition

The starting indolines of formula 4 have either been described hereinabove (i.e. in connection with Examples 145 and 149) or may be obtained in an analogous manner by reaction of the appropriate substituted indoline with the required chloropyrimidine derivative. Thus, the following additional starting materials of formula 4 (R$^6$=NHCH$_3$) were obtained:

| Cpd. No. | B | R$^2$ | Recryst. solvent(s) | m.p. (°C.) | yield (%) |
|---|---|---|---|---|---|
| 4 | 3-Me | Me | EtOAc | 164–165 | 59 |
| 5 | 3-Et | Me | EtOH | 178–180 | 25 |

EXAMPLE 159

A mixture of 4-N-ethylanilino-2-methyl-1-phenylpyrimidin-6-one (0.6 g, 1.76 mM) and phosphorus oxychloride (6 ml) was heated under reflux for 2 hours. The excess phosphorus oxychloride was removed by evaporation. The residue was dissolved in toluene and the solvent evaporated. The process was repeated and the oily residue (containing the corresponding chloride salt of the dichlorophospinoyl derivative of the starting pyrimidinone was added slowly to a stirred solution of methylamine in ethanol (10 ml of 33% w/w). After 16 hours, the solvent was evaporated. 1M Sodium hydroxide solution (10 ml) was added to the residue and the mixture was extracted with ether (2×10 ml). The extracts were dried by filtration through phase-separating paper and treated with ethereal hydrogen chloride. The precipitate was collected by filtration and recrystallised from ethanol/ether to give 4-N-ethylanilino-2-methyl-6-methylamino-1-phenylpyrimidinium chloride (0.364 g), m.p.>330° C.; microanalysis, found: C,64.8; H,6.6; N,15.2; C$_{20}$H$_{23}$N$_4$Cl.0.75H$_2$O requires: C,65.2; H,6.7; N,15.2%; NMR (200 MHz): 1.1(3H,t, CH$_3$), 2.7(3H,s, CH$_3$), 3.8(3H,s, CH$_3$), 4.0(2H,q, CH$_2$), 5.24(1H,s, CH), 7.1–7.3(10H, complex, aromatic H).

The starting material was prepared as follows:

(i) A mixture of 2-methyl-1-phenyl-1,4,5,6-tetrahydropyrimidin-4,6-dione (obtained by the procedure of L. B. Dashkevich, Dokl. Akad. Nauk. SSSR, 1962, 145, 323), (2.02 g, 10 mM) and phosphorus oxychloride (10 ml) was heated at 100° C. for 1 hour. Excess phosphorus oxychloride was removed by evaporation and the residue was added to ice-water with stirring. Sodium carbonate was added to the stirred mixture until there was no more effervescence. The mixture was extracted with methylene chloride (2×20 ml) and the extracts were dried by filtration through phase separation paper. The filtrate was diluted to a volume of 250 ml with methylene chloride and subjected to filtration chromatography on silica (Merck 7736). There was thus obtained 4-chloro-2-methyl-1-phenylpyrimidin-6-one (1.1 g), m.p. 109°–110° C.; NMR (200 MHz): 2.28(3H,s, CH$_3$), 6.5(1H,s, CH), 7.15–7.6(complex, 5 aromatic H).

(ii) A mixture of the above chloropyrimidinone (1.1 g, 50 mM) and N-ethylaniline (1.81 g, 15 mM) was heated at 180° C. (external temperature) under argon for 18 hours. The mixture was cooled and ether (15 ml) was then added. The precipitate of N-ethylaniline hydrochloride was removed by filtration. The filtrate was evaporated and the residue was partitioned between 10% sodium carbonate solution and methylene chloride. The organic layer was dried by filtration through phase separating paper and evaporated. The residue was purified by flash chromatography on silica (Merck 9385) using 3:1 v/v ethyl acetate and hexane to give, after recrystallisation from ethyl acetate/hexane, 4N-ethylanilino-2-methyl-1-phenylpyrimidin-6-one (0.68 g), m.p. 131°–132° C.; NMR (200 MHz): 1.21(3H,t, CH$_3$), 2.1(3H,s, CH$_3$), 3.9(2H,q, CH$_2$), 5.1(1H,s, CH), 7.14–7.55 (complex, 10 aromatic H).

EXAMPLE 160

A mixture of 1,2-dimethyl-4-N-ethylanilinopyrimidin-6-one (1.13 g, 4.65 mM) and phosphorus oxychloride (10 ml) was heated at 100° C. for 4 hours. The excess phosphorus oxychloride was removed by evaporation. The residual gum (containing the corresponding chloride salt of the dichlorophospinoyl derivative of the starting pyrimidinone) was dissolved in ethanol (10 ml). To this solution was added dropwise with stirring and ice-cooling, a 32% w/w solution of methylamine in ethanol (10 ml) so that the temperature did not exceed 30° C. The solution was kept at room temperature for 2 hours after the addition was complete. Solvent was removed by evaporation and the residue was partitioned between 10% w/v sodium carbonate solution (20 ml) and ether (20 ml). The aqueous layer was separated and extracted with methylene chloride (4×10 ml). The combined organic extracts were dried (MgSO$_4$) and evaporated to give a gum (1.3 g) which was crystallised from a mixture of acetone and ether to give 1,2-dimethyl-4-N-ethylanilino-6-methylaminopyrimidinium chloride as a solid (0.81 g), m.p. 202°–203° C.

The starting material was prepared as follows:

(i) 4-Chloro-6-hydroxy-2-methylpyrimidine (1.3 g, 10 mM) and N-ethylaniline (5 ml) were heated to 200° C. under argon for 4 hours. The mixture was cooled to room temperature and treated with ethanol (10 ml). The crystalline solid thus obtained was isolated by filtration, washed with ethanol and dried to give 4-N-ethylanilino-6-hydroxy-2-methylpyrimidine (1.28 g), m.p. 265°-266° C.; NMR (200 MHz): 1.0-1.1(3H,t, $CH_3$), 2.0(3H,s, $CH_3$), 3.9(2H,q, $CH_2$), 4.5(1H,s, CH), 7.2-7.5 (complex, 5 aromatic H), 11.5-11.64(1H,br, NH).

(ii) A mixture of the above anilinopyrimidine (1.15 g, 50 mM), methyl iodide (1.9 ml, 0.03 mmol) and potassium hydroxide flake (0.56 g, 10 mM) in ethanol (50 ml) was heated under reflux for 4 hours. Further portions of potassium hydroxide (0.56 g) and methyl iodide (1.9 ml) were then added and heating continued for an extra 3 hours. Solvent was evaporated and the residue was partitioned between 2M sodium hydroxide (25 ml) and ether (25 ml). The ethereal layer was separated, dried ($MgSO_4$) and the ether evaporated to give 1,2-dimethyl-4-N-ethylanilinopyrimidin-6-one as an oil (1.13 g); NMR (200 MHz): 1.17(3H,t, $CH_3$), 2.45(3H,s, $6H_3$), 3.4(3H,s, $CH_3$), 3.92(2H,q, $CH_2$), 5.05(1H,s,CH), 7.1-7.47(complex, 5 aromatic H).

EXAMPLES 161-186

The general procedure described in Example 1 was repeated but starting from the appropriate 1,2-disubstituted-6-methylpyrimidin-1-one of formula 6 (set out hereinafter) producing in situ the chloride salt of the dichlorophospinoyl derivative of the starting pyrimidinone, which latter is then reacted with N-ethylaniline or N-methylaniline to give the following compounds of formula I (Q.A=phenyl; $R^6=CH_3$; $R^5=H$; $Y^-=Cl^-$):

| Example | $R^1$ | $R^2$ | $R^4$ | M.P. (°C.) | Yield (%) | Recryst. solvent(s) |
|---|---|---|---|---|---|---|
| 161 | 2-MeO-Ph | $NH_2$ | Et | 267-268[a] | +30 | $Me_2CO/Et_2O$ |
| 162 | 4-Me-Ph | $NH_2$ | Et | 215-216[b] | 29 | $Me_2CO$ |
| 163 | 2-Me-Ph | $NH_2$ | Et | 252-253 | 19* | $EtOH/Et_2O$ |
| 164 | 3-MeO-Ph | $NH_2$ | Et | 158-160 | 34 | EtOAc |
| 165 | 4-MeO-Ph | $NH_2$ | Me | 218 | 22* | $Me_2CO/Et_2O$ |
| 166 | Bu | $NH_2$ | Et | 216-217 | 12 | $Me_2CO/Et_2O$ |
| 167 | $Bu^i$ | $NH_2$ | Et | 280-282[c] | +19 | $Me_2CO/Et_2O$ |
| 168 | Bu | $NH_2$ | Me | 235-237[a] | 8 | $Me_2CO/Et_2O$ |
| 169 | $Pr^i$ | $NH_2$ | Et | 213-214 | 26 | $Me_2CO/Et_2O$ |
| 170 | pentyl | $NH_2$ | Et | 199-200 | 28 | $Me_2CO/Et_2O$ |
| 171 | 4-MeO-Ph | NHEt | Et | 176-177[b] | 42 | $Me_2CO/Et_2O$ |
| 172 | 4-MeO-Ph | NHMe | Et | 223-225 | +15 | $EtOH/Et_2O$ |
| 173 | hexyl | NHMe | Et | 148-149 | 45 | $Me_2O/Et_2O$ |
| 174 | $PhCH_2$ | NHMe | Et | 195-196[a] | 66 | $Me_2CO/Et_2O$ |
| 175 | $Bu^i$ | NHMe | Et | 105-108[d] | 27 | $Me_2CO/Et_2O$ |
| 176 | Bu | NHMe | Et | 142-143[c] | 46 | EtOAc |
| 177 | $Pr^i$ | NHMe | Et | 199-200 | 37 | $Me_2CO/Et_2O$ |
| 178 | Pr | NHMe | Et | 212-214 | 22 | $Me_2CO$ |
| 179 | 4-MeO-Ph | NHMe | Me | 226-228 | 46 | $Me_2CO$ |
| 180 | hexyl | NHMe | Me | 156-158 | 41 | $Me_2CO/Et_2O$ |
| 181 | $Bu^i$ | NHMe | Me | 142-146[b] | 21 | $Pr^iOH/Et_2O$ |
| 182 | $PhCH_2$ | NHMe | Me | 208-209[b] | 62 | $Me_2CO/EtOAC$ |
| 183 | Bu | NHMe | Me | 164-165[a] | 56 | $Me_2CO/Et_2O$ |
| 184 | $Pr^i$ | NHMe | Me | 163-164 | 47 | $Me_2CO/Et_2O$ |
| 185 | Pr | NHMe | Me | 215-217 | 18 | $Me_2CO$ |
| 186 | Et | NHMe | Me | 225-227 | 16 | $Pr^iOH/Et_2O$ |

Notes:
* characterised as the iodide salt
+ with decomposition
[a] analyses for 0.5 $H_2O$
[b] analyses for 0.25 $H_2O$
[c] analyses for 1.25 $H_2O$
[d] analyses for 0.75 $H_2O$ The starting 1,2-disubstituted-6-methylpyrimidin-4-ones of formula 6 were obtained in an analogous manner to that described in parts (i)-(iii) of Example 2 that is by reaction of the appropriate 1-substituted-6-methyl-2-methylthiopyrimidin-4-one of the formula 7 (set out hereinafter) with methylammonium acetate, ammonium acetate or ethylammonium acetate, the formula 7 compounds being obtained by methylation of the corresponding thiones of formula 8 (set out hereinafter). The latter thiones were made by analogous procedures to those described in parts (i) and (ii) of Example 3.

The pyrimidin-4-ones of formula 6 had the following properties.

| Formula 6 for Ex. | $R_1$ | $R^2$ | M.P. (°C.) | Yield (%) | Recryst. solvent(s) |
|---|---|---|---|---|---|
| 161 | 2-MeO-Ph | $NH_2$ | 255-257 | 53 | EtOH |
| 162, 165 | 4-Me-Ph | $NH_2$ | 297-298 | 49 | EtOH/hexane |
| 163 | 2-Me-Ph | $NH_2$ | 125-127 | 45 | $EtOH/Et_2O$ |
| 164 | 3-MeO-Ph | NH2 | 258-260 | 42 | EtOH |
| 166, 168 | Bu | NH2 | 186-187 | 38 | — |
| 167 | $Bu^i$ | $NH_2$ | 276-278 | 30 | EtOH |
| 169 | $Pr^i$ | $NH_2$ | 242-243 | 44 | $EtOH/Pr^iOH$ |
| 170 | pentyl | $NH_2$ | 254-256 | 40 | isolated from EtOH |
| 171 | 4-MeO-Ph | NHEt | 220-225 | 34 | EtOAC/EtOH |
| 172 | 4-MeO-Ph | NHMe | 243-245 | 38 | $EtOH/Et_2O$ |
| 173 | hexyl | NHMe | 135-136 | 74 | $Me_2CO/Et_2O$ |
| 174 | $PhCH_2$ | NHMe | 270-271 | 83 | EtOH |
| 175 | $Bu^i$ | NHMe | 135-137 | 53 | — |
| 176 | Bu | NHMe | 224-225 | 80 | washed with $Me_2CO$ |
| 177 | $Pr^i$ | NHMe |  | 53 | $EtOH/Et_2O$ |
| 178 | Pr | NHMe | 202-203 | 81 | MeCN |
| 186 | Et | NHMe | 264-266 | 63 | $EtOH/Et_2O$ |

The methylthio derivatives of formula 7 had the following properties:

| Formula 7 for Example | $R^1$ | M.P. (°C.) | Yield (%) | Recryst. solvent(s) |
|---|---|---|---|---|
| 161 | 2-MeO-Ph | 154-158 | 68 | EtOAc |
| 163 | 2-Me-Ph | 178-179 | 53 | isolated from $CH_2Cl_2$ |
| 164 | 3-MeO-Ph | 173 | 62 | isolated from $CH_2Cl_2$ |
| 166* | Bu | 143-146 | 77 | EtOAc |

-continued

| Formula 7 for Example | $R^1$ | M.P. (°C.) | Yield (%) | Recryst. solvent(s) |
|---|---|---|---|---|
| 167* | $Bu^i$ | 87–89 | 94 | triturated with $Et_2O$ |
| 169* | $Pr^i$ | 152–155 (dec.) | 85 | isolated from EtOAc |
| 170 | pentyl | 157–158 | +68 | isolated from $Me_2CO$ |
| 173* | hexyl | 144–145 | 70 | isolated from $Me_2CO$ |
| 174* | $PhCH_2$ | 78–81 | 58 | toluene |
| 178* | Pr | 85–87 | 72 | isolated from $EtOH/Et_2O$ |
| 186 | Et | 185–187 | 59 | EtOH |

Note:
*also required for other Examples
+ hydriodide salt

The thiones of formula 8 had the following properties:

| Formula 8 for Example | $R^1$ | M.P. (°C.) | Yield (%) | Recrystallisation solvent |
|---|---|---|---|---|
| 161 | 2-MeO-Ph | 232–234 | 56 | EtOH |
| 163 | 2-Me-Ph | 235–237 | 83 | EtOH |
| 164 | 3-MeO-Ph | 225–227 | 12 | EtOH |
| 165* | Bu | 165–166 | 46 | MeOH |
| 166* | $Bu^i$ | 189–191 | 35 | $EtOH/MeOH/H_2O$ |
| 169* | $Pr^i$ | 154–157 | 13 | EtOAc |
| 170 | pentyl | 134–136 | 44 | EtOAc |
| 183* | hexyl | 136–137 | 34 | MeOH |
| 184* | $PhCH_2$ | 210–212 | 55 | EtOH |

Note:
*also required for other Examples

The starting thiones of formula 8 for Examples 178 and 186 were obtained as described by Agai et alia, Period. *Polytech. Chem. Eng.*, 1974, 18, 47 and West German OLS No. 252729 (published 8 Jan 1976).

EXAMPLES 187–188

The general procedure described in Example 1, was repeated but starting from the known compound 1,6-dimethyl-2-methylaminopyrimidin-4-one (Agai et alia, Period. *Polytech. Chem. Eng.*, 1974, 18, 47) and phosphorus oxychloride to produce the corresponding reactive derivative, which derivative was then reacted with the appropriate amine of the formula $Q.A.NHR^4$. There were thus obtained the following compounds of formula I ($R^1=R^6=CH_3$):

(Example 187): 1,6-dimethyl-2-methylamino-4-(N-ethyl-2-(2-methoxyphenoxyethylamino)pyrimidinium chloride, as a solid, m.p. 170°–171° C. (recrystallised from acetone) in 40% yield (partial hydrate: 0.5 $H_2O$; and (Example 188): 1,6-dimethyl-2-methylamino-4-(N-methyl-2-phenylethylamino)pyrimidium bromide (mixed with 33% chloride), as a solid, m.p. 219°–221° C. (recrystallised from 2-propanol/ether) in 445 yield.

EXAMPLES 189–190

Using a similar procedure to that described in Example 47 but using the appropriate amine of the formula $Q.A.NHR^4$, there were obtained the following compounds of formula I ($R^1=R^6=CH_3$):

(Example 189): 2-amino-1,6-dimethyl-4-(N-methyl-2-phenylethylamino)pyrimidium iodide, as a solid, m.p. 168°–169° C. (recrystallised from 2-propanol/ether) in 45% yield;

(Example 190): 2-amino-1,6-dimethyl-4-(N-ethyl-2-(2-methoxyphenoxyethlamino)pyrimidinium iodide, as a solid, m.p. 138°–140° C. (recrystallised from acetone/water) in 23% yield; and (Example 191): 2-amino-4-(1,2,3,4-tetrahydroisoquinol-2-yl)-1,6-dimethylpyrimidinium bromide, as a solid, m.p. 275°–276° C. (recrystallised from ethanol)in 12% yield (partial hydrate: 0.25 $H_2O$).

EXAMPLE 192

Using a similar procedure to that described in Example 160 but using dimethylamine instead of methylamine, there was obtained 1,2-dimethyl-6-dimethylamino-4-N-ethlanilinopyrimidinium chloride as a glassy solid in 76% yield; NMR(200 MHz; $d_6$-DMSO): 1.16(3H, t, $CH_2CH_3$), 2.64(3H, s, pyrimidine-2-$CH_3$), 2.8[6H, s, $N(CH_3)_2$], 3.65(3H, s, pyrimidine-1-$CH_3$), 4.06(2H, q, $CH_2CH_3$), 5.54(1H, br s, pyrimidine-5H), 7.3–7.65(5H, complex, phenyl).

EXAMPLE 193

The following illustrate representative pharmaceutical dosage forms containing a compound of formula I, or an alternative non-toxic salt thereof, which may be used for therapeutic or prophylactic purpose in humans:

| (a) Tablet | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone 5% w/v paste) | 2.25 |
| Magnesium stearate | 3.0 |
| (b) Capsule | mg/capsule |
| Compound X | 10 |
| Lactose Ph.Eur | 488.5 |
| Magnesium stearate | 1.5 |

"Compound X" stands for a typical compound of the formula I or an alternative non-toxic salt thereof such as is described in any preceding Example herein.

The above formulations may be obtained by conventional procedures well known in the pharmaceutical art. The tablets may be coated by conventional means, for example to modify dissolution/disintegration characteristics or improve palatability or stability. For example, a coating of cellulose acetate phthalate may be applied to the tablets to provide a formulation which predominantly releases the majority of the active ingredient in or near the lower alimentary tract.

CHEMICAL FORMULAE

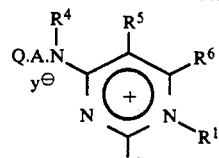

I

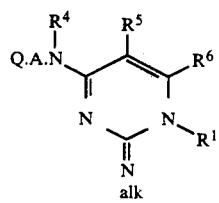

Ia

-continued
CHEMICAL FORMULAE
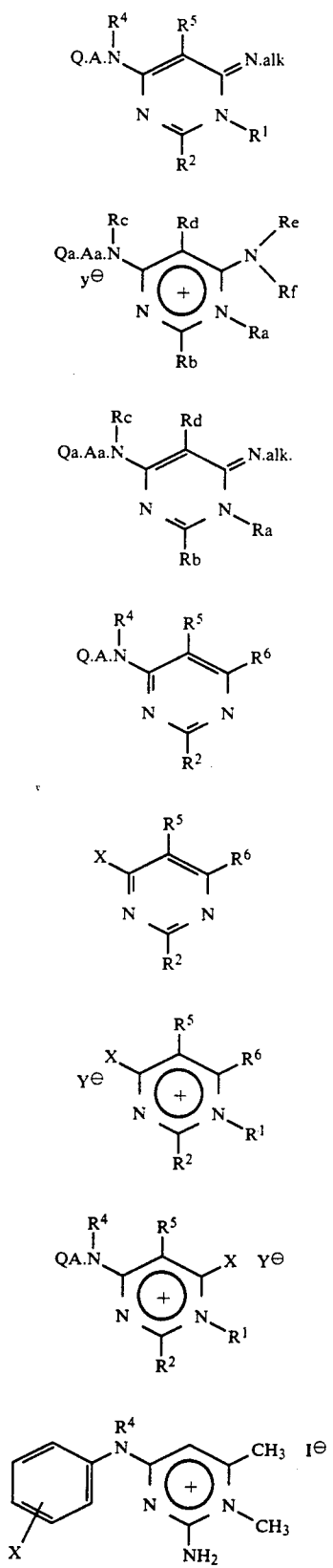
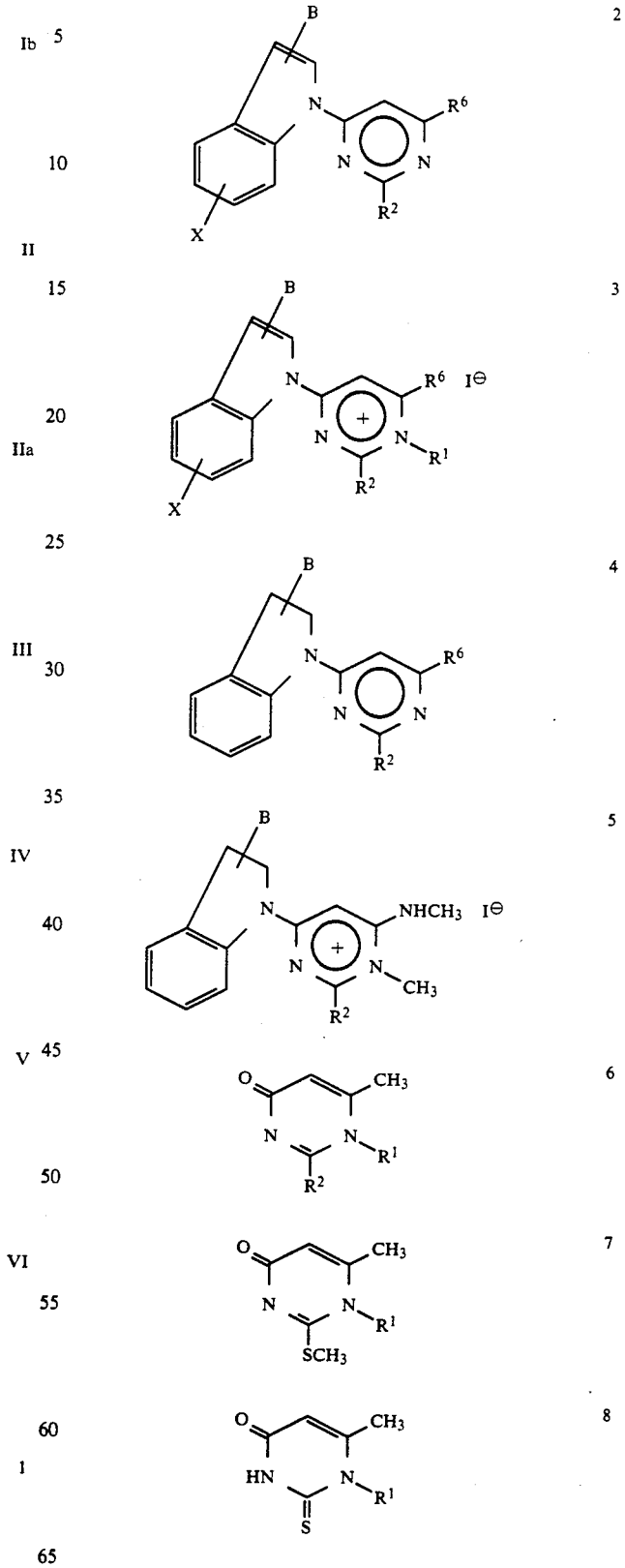
What is claimed is:
1. An aminopyrimidine derivative of the formula I:

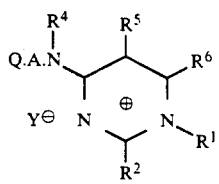

wherein $R^1$ is (1-100C)alkyl, (3-6C)alkenyl, (4-7C)cycloalkyl, phenyl, phenyl(1-4C)alkyl or (3-6C)cycloalkyl-(1-4C)alkyl;

one of $R^2$ and $R^6$ is a basic group selected from amino, (1-6C)alkylamino, dialkylamino of up to eight carbon atoms, pyrrolidino, piperidino and morpholino; and the other of $R^2$ and $R^6$ is hydrogen, (1-6C)alkyl, (3-6C)alkenyl, (1-4C)alkoxy(1-4C)alkyl, phenyl, phenyl(1-4C)alkyl, (3-6C)cycloalkyl or (3-6C)cycloalkyl-(1-4C)alkyl;

or both of $R^2$ and $R^6$ are basic groups independently selected from the above defined basic groups; and $R^5$ is hydrogen, (1-4C)alkyl or (3-6C)alkenyl;

or $R^2$ is a basic group as defined above, and $R^5$ and $R^6$ together form (3-6C)alkylene or, together with the appendant carbon atoms of the pyrimidine ring, complete a benzene ring;

$R^4$ is hydrogen, (3-6C)cycloalkyl-(1-4C)alkyl, (1-6C)alkyl, (3-6C)alkenyl, (3-6C)alkynyl or phenyl(-1-4C)alkyl; or $R^4$ is a (1-4C)alkylene or (2-4C)alkenylene linked to the nitrogen atom of the group Q.A.N—, either of which linking groups may optionally bear a (1-4C)alkyl, phenyl or phenyl(1-4C)alkyl substituent and either of which linking groups thereby completing a ring including two adjacent carbon atoms of Q, the carbon atoms of A and the adjacent nitrogen atom of the group —A.N—; A is a direct bond to the the group —N($R^4$)— or is (1-6C)alkylene or is oxy(2-6C)alkylene in which the oxy group is at least 2 carbon atoms away from the group —N($R^4$)—; Q is a pyridyl, furyl, thienyl or phenyl moiety;

Y is a physiologically acceptable anion; and wherein any one or more of said phenyl or benzene moieties may optionally be unsubstituted or bear one or more substituents independently selected from halogeno, (1-4C)alkyl, (3-6C)alkenyl, (1-4C)alkoxy, cyano, trifluoromethyl, nitro, carboxy, (1-4C)alkylamino, dialkylamino of up to six carbon atoms, (1-4C)alkylthio, (1-4C)alkylsulphinyl, (1-4C)alkylsulphonyl and (1-4C)alkylenedioxy;

but excluding those compounds in which:

(a) $R^1$ is alkyl, $R^2$ is amino or alkylamino, $R^4$ is hydrogen or alkyl, $R^5$ is hydrogen or alkyl, $R^6$ is hydrogen or phenyl optionally bearing an alkyl or alkoxy substituent, A is a direct link and Q is phenyl optionally bearing an alkyl or alkoxy substituent;

(b) $R^1$ is methyl or ethyl, $R^2$ is amino, $R^4$ and $R^5$ are hydrogen, $R^6$ is methyl, and Q.A— is unsubstituted phenyl; or (c) $R^1$, $R^5$ and $R^6$ are methyl, $R^2$ is methylamino, $R^4$ is hydrogen and Q.A- is 3,5-dimethylphenyl; $R^2$ is methylthio, $R^1$, $R^4$ and $R^6$ are methyl; and, in any of which, Y has the meaning stated above.

2. A compound as claimed in claim 1 wherein:

$R^1$ is methyl, ethyl, propyl, butyl, pentyl, heptyl, allyl, but-2-enyl, but-3-enyl, 2-methyl-2-propenyl, pentenyl, cyclopropyl, cyclobutyl, cyclopentyl, cyclohexyl, cycloheptyl, phenyl, benzyl, 1-phenylethyl, 2-phenylethyl, cyclopropyl-methyl, cyclopentyl-methyl, cyclohexyl-methyl or 2-(cyclohexyl)ethyl;

one of $R^2$ and $R^6$ is a basic group selected from amino, methylamino, ethylamino, propylamino, butylamino, dimethylamino, diethylamino, methylpropylamino, dipropylamino, pyrrolidino, piperidino and morpholino; and the other of $R^2$ and $R^6$ is hydrogen, methyl, ethyl, propyl, butyl, isobutyl, allyl, but-2-enyl, but-3-enyl, 2-methyl-2-propenyl, pentenyl, methoxymethyl, ethoxymentyl, 2-methoxyethyl, 2-ethoxyethyl, phenyl, benzyl, 1-phenylethyl, 2-phenylethyl, cyclopropyl, cyclobutyl, cyclopentyl, cyclohexyl, cyclopropyl-methyl, cyclopentyl-methyl, cyclohexyl-methyl or 2-(cyclohexyl)ethyl; or both of $R^2$ and $R^6$ are basic groups independently selected from the above defined basic groups; and $R^5$ is hydrogen, methyl, ethyl, propyl, isopropyl, allyl, but-2-enyl, but-3-enyl or pentenyl; or $R^2$ is a basic group as defined above, and $R^5$ and $R^6$ together form trimethylene, tetramethylene, pentamethylene or a group of the formula —CH$_2$.C(CH$_3$)$_2$.CH$_2$— or —CH$_2$.C(CH$_3$)$_2$.CH$_2$.CH$_2$—, $R^5$ and $R^6$ together with the appendant carbon atoms of the pyrimidine ring, complete a benzene ring;

$R^4$ is hydrogen, cyclopropyl-methyl, cyclopentyl-methyl, cyclohexyl-methyl or 2-(cyclohexyl)ethyl, methyl, ethyl, propyl, isopropyl, butyl, isobutyl, sec-butyl, pentyl, allyl, but-2-enyl, but-3-enyl, pentenyl, prop-2-ynyl, but-2-ynyl, benzyl, 1-phenylethyl and 2-phenylethyl; or $R^4$ is methylene, ethylidene, ethylene, isopropylidene, trimethylene, tetramethylene, vinylene or 1,3-propenylene linked to the nitrogen atom of the group Q.A.N-, any of which linking groups may optionally bear a methyl, ethyl, propyl, butyl, phenyl, benzyl, 1-phenylethyl or 2-phenylethyl substituent and any of which linking groups thereby completing a ring including two adjacent carbon atoms of Q, the carbon atoms of A and the adjacent nitrogen atom of the group —A.N—;

A is a direct bond to the the group —N($R^4$)— or is methylene, ethylene, trimethylene, tetramethylene, any of which may optionally bear one or two methyl substituents, or A is oxyethylene, oxytrimethylene, methyleneoxyethylene or ethyleneoxyethylene, any of which may optionally bear one or two methyl substituents;

Q has the meanings defined in claim 1; Y is a physiologically acceptable anion;

and wherein any one or more of said phenyl or benzene moieties may optionally be unsubstituted or bear one or more substituents independently selected from fluoro, chloro, bromo, methyl, ethyl, propyl, allyl, 2-methyl-2-propenyl, methoxy, ethoxy, propoxy, cyano, trifluormethyl, nitro, carboxy, methylamino, ethylamino, dimethylamino, diethylamino, methylthio, ethylthio, methylsulphinyl, ethylsulphinyl, methylsulphonyl, ethylsulphonyl, methylenedioxy and isopropylidenedioxy.

3. A compound as claimed in claim 1 wherein $R^4$ is (1-6C)alkyl, A is a direct link and Q is selected from phenyl, 4-chlorophenyl, 4-methylphenyl, 2-nitrophenyl, 2-methylphenyl, 2-carboxyphenyl, 2-methoxyphenyl, 4-methylthiophenyl, 2,5-dinitrophenyl, 2,5-dimethylphenyl, 3,5-dimethylphenyl, 3,5-dichlorophenyl, 3,5- dibromophenyl and 3,5-dimethoxyphenyl; or the group of the formula Q.A.N(R⁴)- is selected from 1-indolyl, 3-methyl-1-indolyl, 3-ethyl-1-indolyl, 3-propyl-1-indolyl, 5-bromo-1-indolyl, 5-chloro-1-indolyl, 5-fluoro-1-indolyl, 5-methyl-1-indolyl, 5-methoxy-1-indolyl, 1-indolinyl, 3-methyl-1-indolinyl, 3-ethyl-1-indolinyl, and 3-isopropyl-1-indolinyl.

4. A compound of the formula II:

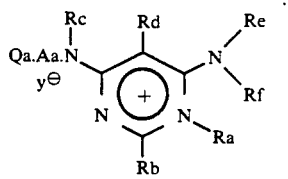

wherein: Ra is (1-10C)alkyl, (3-6C)alkenyl, phenyl, phenyl(1-4C)alkyl, (3-6C)cycloalkyl or (3-6C)cycloalkyl-(1-4C)alkyl; Rb is (1-6C)alkyl, phenyl, phenyl(1-4-C)alkyl, (3-6C)cycloalkyl or (3-6C)cycloalkyl-(1-4-C)alkyl, amino, (1-4C)alkylamino or dialkylamino of up to 6 carbon atoms; Rc is hydrogen, (3-6C)cycloalkyl-(1-4C)alkyl, (1-6C)alkyl, (3-6C)alkenyl, (3-6C)alkynyl or phenyl(1-4C)alkyl; or Rc is (1-4C)alkylene or (2-4C)alkenylene linked to the nitrogen atom of the group Qa.Aa.N—, either of which linking groups may optionally bear a (1-4C)alkyl, phenyl or phenyl(1-4-C)alkyl substituent and either of which linking groups thereby completes a ring including two adjacent carbon atoms of Qa, the atoms of Aa and the nitrogen of group —Aa.N—; Rd is hydrogen; Re and Rf are independently selected from hydrogen and (1-4C)alkyl, or together form (3-6C)alkylene; Qa is phenyl or pyridyl; Aa is a direct bond to the group —NRc—; Y is a physiologically acceptable anion; and wherein any one or more of said phenyl moieties may optionally be unsubstituted or bear one or more substituents independently selected from halogeno, trifluoromethyl, cyano, nitro, (1-4C)alkyl and (1-4C)alkoxy.

5. A compound as claimed in claim 4 in which Ra is methyl, ethyl, butyl, phenyl or cyclohexyl, Qa is phenyl optionally substituted as defined in claim 4, and Rc is methyl or ethyl.

6. A compound of the formula

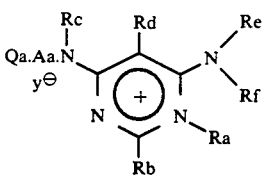

wherein Qa is phenyl; Aa is a direct bond to the group —N(Rc)—; Ra is (1-7C)alkyl or (3-6C)alkenyl; Rb is (1-4C)alkyl; Rc is hydrogen, (1-6C)alkyl, (3-6C)cycloalkylmethyl or (3-6C)alkenyl; or Rc is (2-4C)alkylene or (2-4C)alkenylene completing a ring including two adjacent carbon atoms of benzene ring Qa and the nitrogen atom of the group —N(Rc)—; Rd is hydrogen or (1-4C)alkyl; Re and Rf are independently selected from hydrogen and (1-4C)alkyl; Y is a physiologically acceptable anion; and wherein benzene ring Qa may optionally be unsubstituted or bear one or two substituents independently selected from halogeno, (1-4C)alkyl and (1-4C)alkoxy.

7. A compound as claimed in claim 6 wherein Qa is phenyl; Aa is a direct bond to the group —N(Rc)—; Ra is methyl or ethyl; Rb is methyl, ethyl or propyl; Rc is ethyl; or Rc is ethylene or vinylene completing an indoline or indole ring, repectively, including two adjacent carbon atoms of benzene ring Qa and the nitrogen atom of the group —N(Rc)—; Rd is hydrogen or methyl; Re is hydrogen and Rf is methyl or ethyl; Y is a physiologically acceptable anion; and wherein benzene ring Qa may optionally be unsubstituted or bear one or two substituents independently selected from fluoro, chloro, bromo, methyl and methoxy.

8. A non-ionic compound having the structure Ia or Ib:

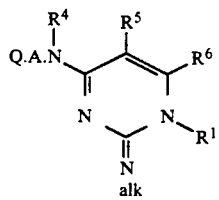

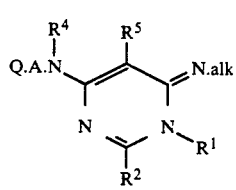

(or a tautomeric structure thereof when R⁴ is hydrogen or when the other of R² and R⁶ is amino or alkylamino), wherein "alk" stands for (1-6C)alkyl and wherein:

R¹ is (1-10C)alkyl, (3-6C)alkenyl, (4-7C)cycloalkyl, phenyl, phenyl(1-4C)alkyl or (3-6C)cycloalkyl-(1-4C)alkyl;

each of R² and R⁶ is a basic group selected from amino, (1-6C)alkylamino, dialkylamino of up to eight carbon atoms, pyrrolidino, piperidino, morpholino, or is selected from hydrogen, (1-6C)alkyl, (3-6C)alkenyl, (1-4C)alkoxy(1-4C)alkyl, phenyl, phenyl(1-4C)alkyl, (3-6C)cycloalkyl or (3-6C)cycloalkyl-(1-4C)alkyl; and R⁵ is hydrogen, (1-4C)alkyl or (3-6C)alkenyl;

or R⁵ and R⁶ together form (3-6C)alkylene or, together with the appendant carbon atoms of the pyrimidine ring, complete a benzene ring;

R⁴ is hydrogen, (3-6C)cycloalkyl-(1-4C)alkyl, (1-6C)alkyl, (3-6C)alkenyl, (3-6C)alkynyl or phenyl(1-4C)alkyl; or R⁴ is a (1-4C)alkylene or (2-4C)alkenylene linked to the nitrogen atom of the group Q.A.N—, either of which linking groups may optionally bear a (1-4C)alkyl, phenyl or phenyl(1-4C)alkyl substituent and either of which linking groups thereby completing a ring including two adjacent carbon atoms of Q, the carbon atoms of A and the adjacent nitrogen atom of the group —A.N—; A is a direct bond to the the group —N(R⁴)— or is (1-6C)alkylene or is oxy(2-6C)alkylene in which the oxy group is at least 2 carbon atoms away from the group —N(R⁴)—; Q is a pyridyl, furyl, thienyl or phenyl moiety;

and wherein any one or more of said phenyl or benzene moieties may optionally be unsubstituted or bear one or more substituents independently selected from halogeno, (1-4C)alkyl, (3-6C)alkenyl, (1-4C)alkoxy, cyano, trifluoromethyl, nitro, carboxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy;

but excluding those compounds in which:

(a) $R^1$ is alkyl, $R^2$ is amino or alkylamino, $R^4$ is hydrogen or alkyl, $R^5$ is hydrogen or alkyl, $R^6$ is hydrogen or phenyl optionally bearing an alkyl or alkoxy substituent, A is a direct link and Q is phenyl optionally bearing an alkyl or alkoxy substituent;

(b) $R^1$ is methyl or ethyl, $R^2$ is amino, $R^4$ and $R^5$ are hydrogen, $R^6$ is methyl, and Q.A— is unsubstituted phenyl; or (c) $R^1$, $R^5$ and $R^6$ are methyl, $R^2$ is methylamino, $R^4$ is hydrogen and Q.A— is 3,5-dimethylphenyl.

9. A compound of the formula IIa:

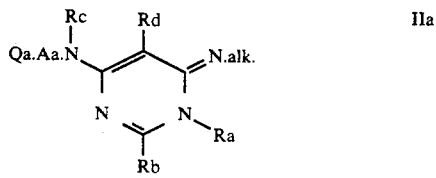

wherein: Ra is (1–10C)alkyl, (3–6C)alkenyl, phenyl, phenyl(1–4C)alkyl, (3–6C)cycloalkyl or (3–6C)cycloalkyl-(1–4C)alkyl; Rb is (1–6C)alkyl, phenyl, phenyl(1–4C)alkyl, (3–6C)cycloalkyl, (3–6C) cycloalkyl-(1–4C)alkyl, amino, (1–4C)alkylamino or dialkylamino of up to 6 carbon atoms; Rc is hydrogen, (3–6C)cycloalkyl-(1–4C)alkyl, (1–6C)alkyl, (3–6C)alkenyl, (3–6C)alkynyl or phenyl(1–4C)alkyl; or Rc is (1–4C)alkylene or (2–4C)alkenylene linked to the nitrogen atom of the group Qa.Aa.N—, either of which linking groups may optionally bear a (1–4C)alkyl, phenyl or phenyl(1–4C)alkyl substituent and either of which linking groups thereby completes a ring including two adjacent carbon atoms of Qa, the atoms of Aa and the nitrogen of group —Aa.N—; Rd is hydrogen; Qa is phenyl or pyridyl; and Aa is a direct bond to the group —NRc—; and wherein any one or more of said phenyl moieties may optionally by unsubstituted or bear one or more substituents independently selected from halogeno, trifluoromethyl, cyano, nitro, (1–4C)alkyl and (1–4C)alkoxy.

10. A compound as claimed in claims 1, 4 or 6 in which Y is selected from halide, sulphate, fluoroborate, phosphate, nitrate, acetate, benzoate, butyrate, citrate, tartrate, dibenzoyltartrate, fumarate, trifluoroacetate, methosulphate and p-toluenesulphonate.

11. A compound of the formula I as claimed in claim 1 wherein Y is a halide ion and the pyrimidinium counter-cation is selected from 1,6-dimethyl-2-methylamino-4-N-methylanilinopyrimidinium, 1,2-dimethyl-6-methylamino-4-N-ethylanilinopyrimidinium, 1,2-dimethyl-4-(1-indolyl)-6-methylaminopyrimidinium; 1,2-dimethyl-4-(3-methyl-1-indolyl)-6-methylaminopyrimidinium; 1,2-dimethyl-4-(3-ethyl-1-indolyl)-6-methylaminopyrimidinium; 2-ethyl-4-(3-ethyl-1-indolyl)-1-methyl-6-methylaminopyrimidinium; 1,2-dimethyl-6-methylamino-4-(3-propyl-1-indolyl)-pyrimidinium; 1,2-dimethyl-4-(3-methyl-1-indolinyl)-6-methylaminopyrimidinium iodide; and 1,2-dimethyl-4-(3-ethyl-1-indolinyl)-6-methylaminopyrimidinium.

12. The compound 1,2-dimethyl-6-methylamino-4-N-ethylanilinopyrimidinium chloride or iodide.

13. The compound 1,2-dimethyl-6-methylimino-4-N-ethylanilinopyrimidine.

14. An aminopyridine which is 2-methyl-6-methylamino-4-N-ethylanilinopyrimidine.

15. A pharmaceutical composition suitable for modulating the action of the sino-arial node comprising an active ingredient selected from a compound of the formula I as claimed in claim 1, a non-ionic form thereof having the formula Ia or Ib (or a tautomeric form thereof) as claimed in claim 8, and a non-ionic form of said formula I compound having the formula IIa as claimed in claim 9; together with or in admixture with a pharmaceutically acceptable diluent or carrier.

16. A method of modulating the action of the sino-atrial node in a warm-blooded animal requiring such treatment which comprises administering to said animal an effective amount of a phamacologically active agent selected from the group consisting of a compound of the formula I as claimed in claim 1, a non-ionic form thereof having the formula Ia or Ib (or a tautomeric form thereof) as claimed in claim 8, and a non-ionic form of said formula I compound having the formula IIa as claimed in claim 9.

* * * * *